United States Patent [19]

Edoga

[11] Patent Number: 5,591,228
[45] Date of Patent: Jan. 7, 1997

[54] METHODS FOR TREATING ABDOMINAL AORTIC ANEURYSMS

[76] Inventor: John K. Edoga, 10 Franklin Pl., Morristown, N.J. 07960

[21] Appl. No.: 437,368

[22] Filed: May 9, 1995

[51] Int. Cl.$^6$ .................................................... A61F 2/06
[52] U.S. Cl. .................................. 623/1; 623/2; 623/11; 623/12; 606/153; 606/194; 606/198
[58] Field of Search ............................. 623/1, 2, 11, 12; 606/108, 194, 195, 198, 151–158; 128/898; 600/36

[56] References Cited

U.S. PATENT DOCUMENTS

| | | |
|---|---|---|
| 4,140,126 | 2/1979 | Choudhury . |
| 4,577,631 | 3/1986 | Kreamer . |
| 4,592,754 | 6/1986 | Gupte et al. . |
| 4,617,932 | 10/1986 | Kornberg . |
| 4,787,899 | 11/1988 | Lazarus . |
| 4,820,298 | 4/1989 | Leveen et al. . |
| 4,896,670 | 1/1990 | Crittenden . |
| 4,994,071 | 2/1991 | MacGregor . |
| 5,037,392 | 8/1991 | Hillstead . |
| 5,061,275 | 10/1991 | Wallsten et al. . |
| 5,064,435 | 11/1991 | Porter . |
| 5,078,720 | 1/1992 | Burton et al. . |
| 5,104,399 | 4/1992 | Lazarus . |
| 5,116,318 | 5/1992 | Hillstead . |
| 5,116,365 | 5/1992 | Hillstead . |
| 5,123,917 | 6/1992 | Lee . |
| 5,192,297 | 3/1993 | Hull . |
| 5,197,476 | 3/1993 | Nowacki et al. . |
| 5,197,977 | 3/1993 | Hoffman, Jr. et al. . |
| 5,201,757 | 4/1993 | Heyn et al. . |
| 5,207,695 | 5/1993 | Trout, III . |
| 5,211,658 | 5/1993 | Clouse . |
| 5,211,683 | 5/1993 | Maginot .................................. 128/898 |
| 5,219,355 | 6/1993 | Parodi et al. . |
| 5,234,457 | 8/1993 | Anderson . |
| 5,250,069 | 10/1993 | Nobuyoshi et al. . |
| 5,250,070 | 10/1993 | Parodi . |
| 5,263,932 | 11/1993 | Jang . |
| 5,282,824 | 2/1994 | Gianturco . |
| 5,290,295 | 3/1994 | Querals et al. . |
| 5,299,575 | 4/1994 | Sandridge . |
| 5,316,023 | 5/1994 | Palmaz et al. . |
| 5,330,528 | 7/1994 | Lazim . |
| 5,334,142 | 8/1994 | Paradis . |
| 5,342,387 | 8/1994 | Summers . |
| 5,354,308 | 10/1994 | Simon et al. . |
| 5,360,443 | 11/1994 | Barone et al. . |
| 5,370,683 | 12/1994 | Fontaine . |
| 5,382,261 | 1/1995 | Palmaz . |
| 5,387,235 | 2/1995 | Chuter .......................................... 623/1 |
| 5,489,295 | 2/1996 | Pipliani et al. ............................. 623/1 |

FOREIGN PATENT DOCUMENTS

| | | |
|---|---|---|
| 0461791 | 6/1991 | European Pat. Off. . |
| 0556850 | 2/1993 | European Pat. Off. . |
| 9300867 | 1/1993 | WIPO . |

OTHER PUBLICATIONS

"Guidelines for development and use of transluminally palced endovascular prosthetic grafts in the arterial system", Journal of Vascular Surgery, vol. 21, No. 4, pp. 670–685 (Apr. 1995).

"Cardiovascular Devices and the Food and Drug Administration", Circulation, vol. 89, No. 4, pp. 1903–1904 (Apr. 1994).

"The Role of Clinical Trials in the Food and Drug Administration Approval Process for Cardiovascular Devices", Circulation, vol. 89, No. 4, pp. 1900–1902 (Apr. 1994).

*Primary Examiner*—John G. Weiss
*Assistant Examiner*—Francis K. Cuddihy
*Attorney, Agent, or Firm*—Lerner, David, Littenberg, Krumholz & Mentlik

[57] ABSTRACT

The present invention provides methods for treating conditions such as abdominal aortic aneurysms and the like which involve the direct placement of a bifurcated graft in the afflicted area. The surgical procedures can be performed proximally, from above the junction of the abdominal aorta and the renal arteries, or distally through the iliac arteries. Particularly preferred methods include a plurality of entry points made both above and below the afflicted area.

26 Claims, 14 Drawing Sheets

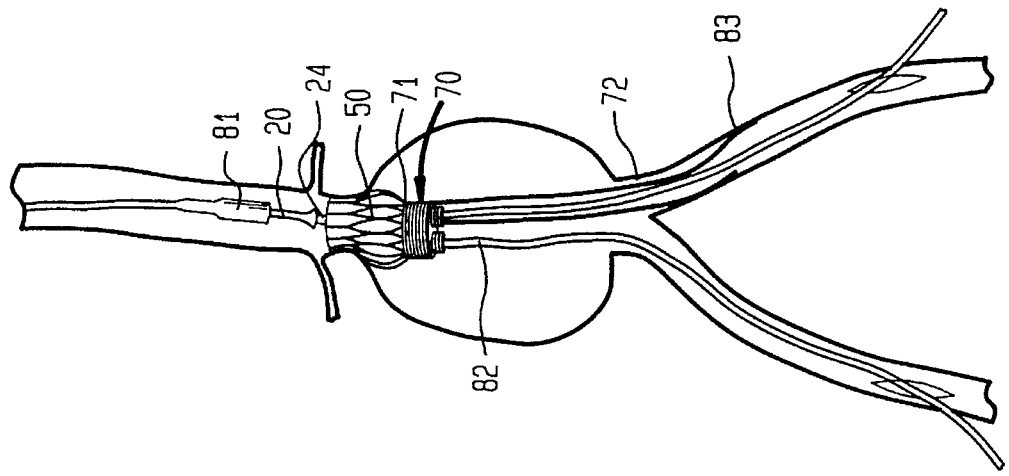
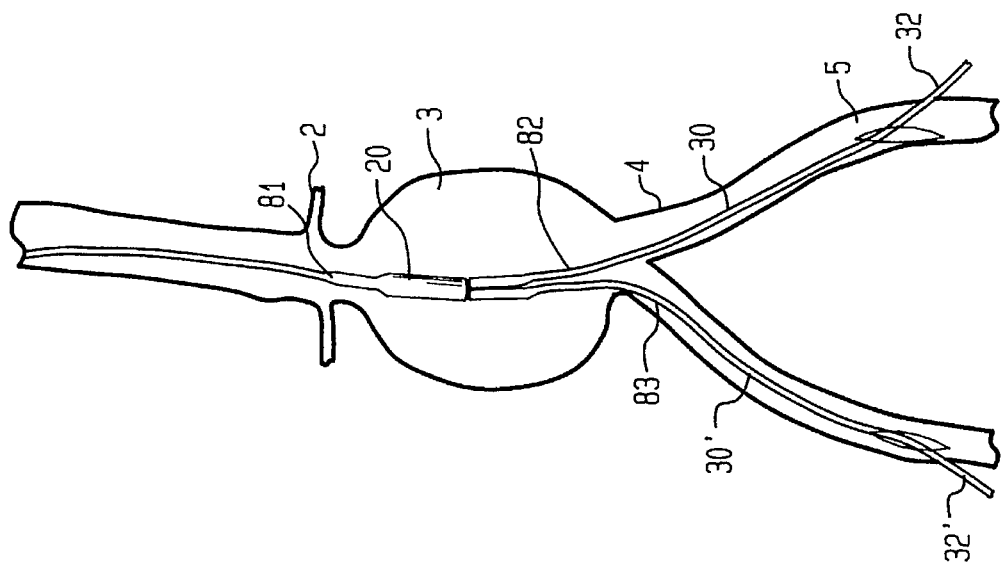

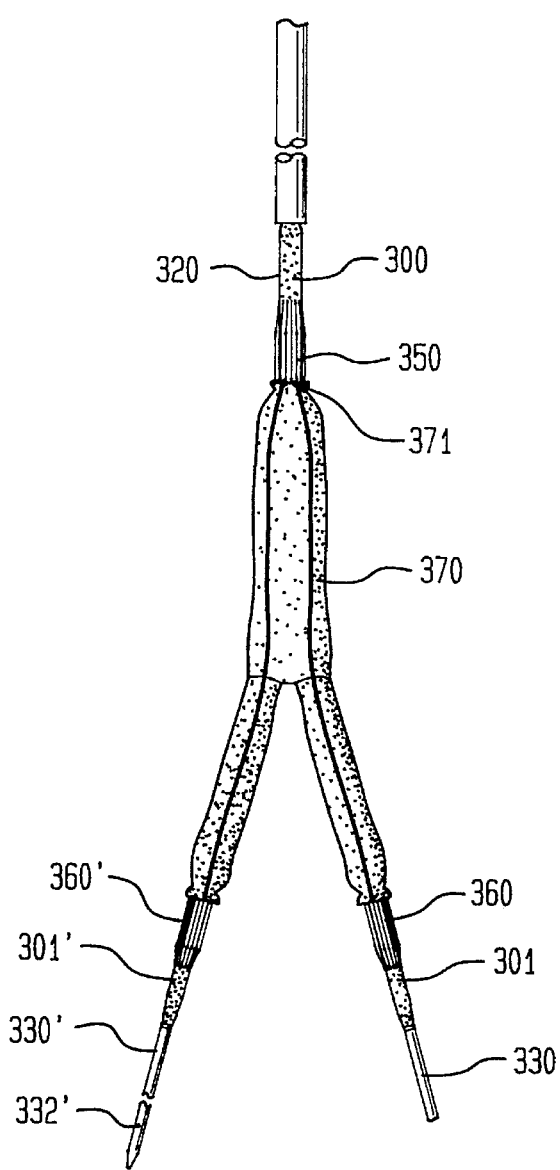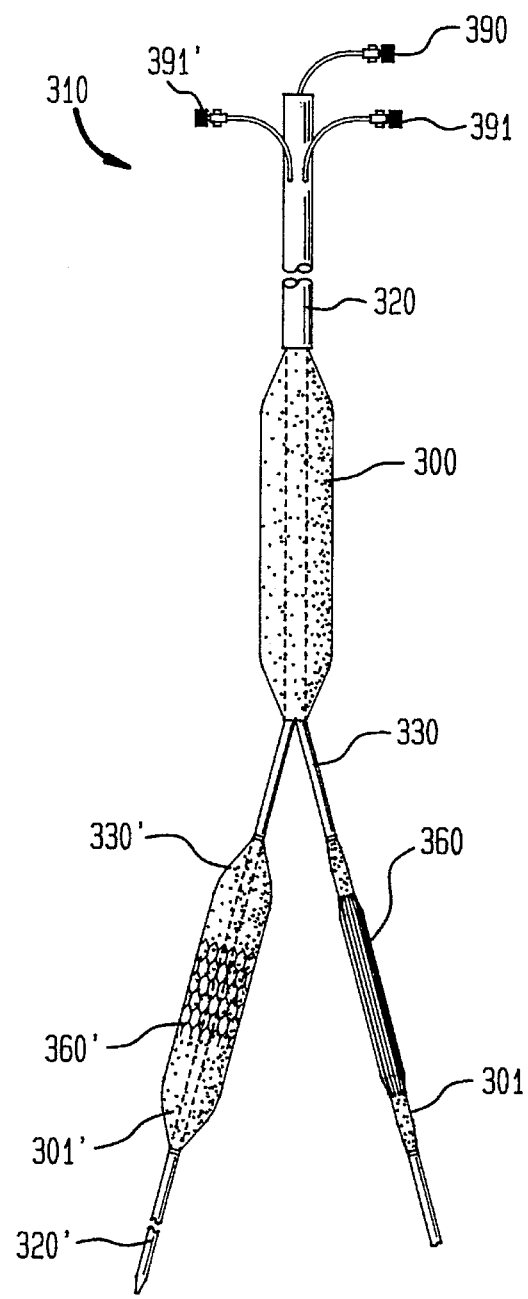

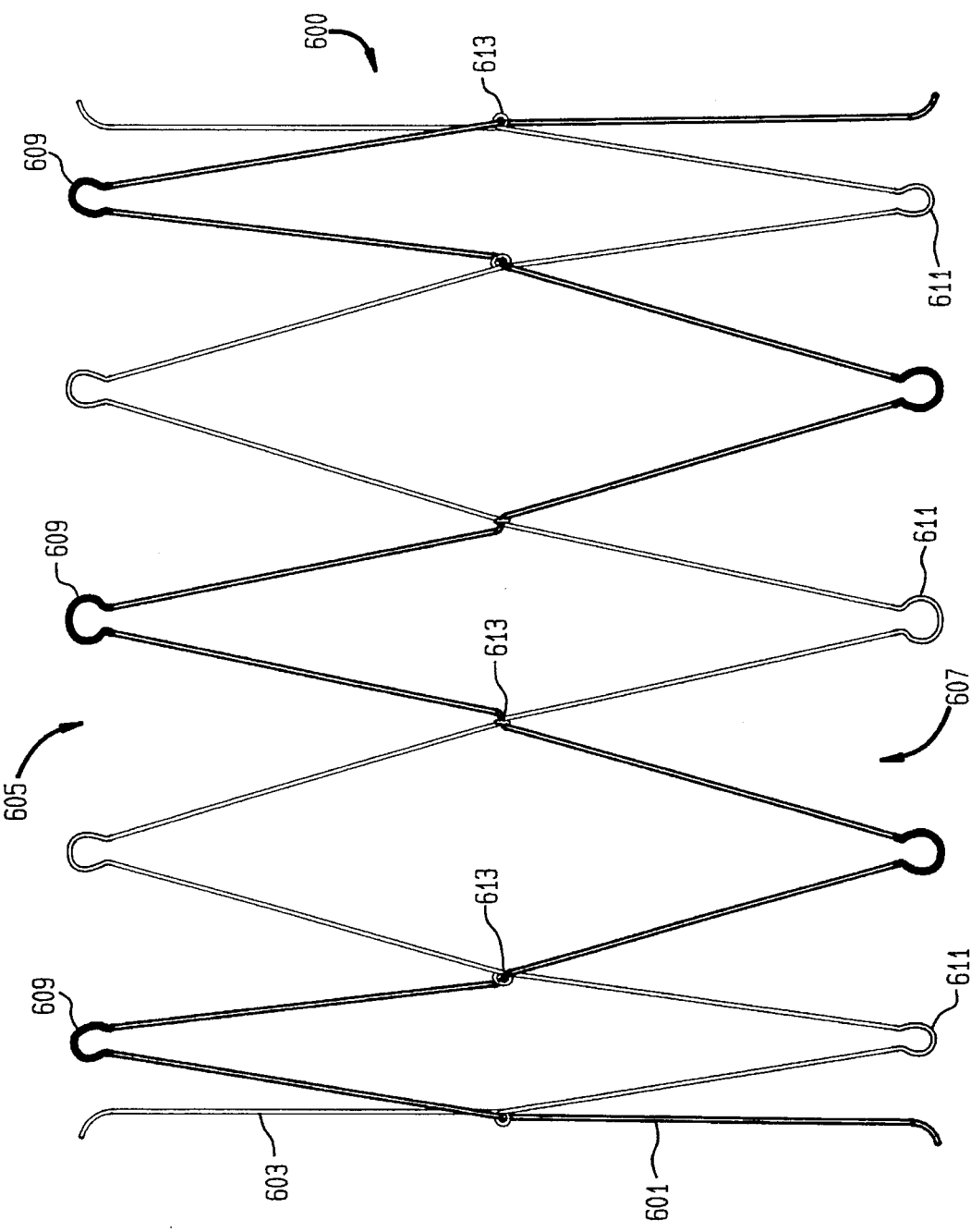

METHODS FOR TREATING ABDOMINAL AORTIC ANEURYSMS

FIELD OF THE INVENTION:

The present invention relates to the field of intra-aortic surgery and methods for accomplishing same as well as devices to assist in the delivery of bifurcated abdominal aortic grafts.

BACKGROUND OF THE INVENTION:

There are several medical conditions which currently require surgery and/or the use of an abdominal aortic graft. These conditions include: abdominal aortic aneurysms, aortic and iliac occlusive disease following balloon angioplasty and aorta-distal arterial embolization. Each of these conditions most commonly affects the aorta immediately below the take off or junction with the renal arteries through and including the area where the aorta divides into the common iliac arteries.

For illustrative purposes, consider a patient having an abdominal aortic aneurysm. An aneurysm is defined as a sac formed by localized dilatation of the aorta. Aneurysms can lead to occlusion and more notably rupture of the arterial wall and thus unconfined bleeding into the abdomen. If left untreated, the patient may die of internal bleeding.

One method of treating this disorder is through the use of an arterial replacement. However, even though the mortality rate for elective aneurysm resection is usually less than 5%, the morbidity of the needed surgery is quite severe. The average hospital stay is ten to fourteen days at a total cost of tens of thousands of dollars. For ruptured aneurysms, the hospital mortality rate is approximately 75% with greater than $2/3$ of the deaths occurring during surgery or within a few hours after surgery. For survivors, the morbidity includes limb and bowel loss and renal failure requiring life long dialysis. When an aortic aneurysm ruptures, resource consumption rises astronomically. There are also a great number of patients in whom co-morbid factors constitute relative or absolute contraindications to this type of surgery such as patients with severe coronary artery disease or pulmonary insufficiency.

Another technique involves the insertion of a graft of material within the existing aorta and anchoring the graft in place such that it acts to carry blood through the afflicted portion of the aorta. This is analogous to fixing a leaking pipe by placing another pipe of smaller diameter within the existing pipe and, in essence, bypassing the afflicted area of the aorta. However, the technique does have some problems, including difficulty in accurately sizing and delivering the graft in a bifurcated blood vessel. One problem, for example, is that until surgery begins, it is often difficult to know exactly the length of a graft which will actually be required to reach from the affected area of the aorta just below the renal arteries down to and through the iliac arteries. While surgeons can estimate the necessary length, a graft which is too long may buckle or kink once flow is restored. If, on the other hand, the graft is too short then when a stent is released to anchor the graft in place, it may expand in an already weakened portion of the aortic or iliac arteries and cause rupture, leakage or other complications.

Perhaps the biggest problem, however, is getting both of the lower or iliac ends of the graft, which are to be disposed in the right and left iliac arteries, properly aligned and positioned while, at the same time, controlling the placement of the upper or aortic end of the graft. While a number of techniques have been suggested, the most common techniques use two guide wires which are inserted through the common femoral artery of one leg up into the body. A first guide wire is inserted through the common femoral artery in one leg such that its free end dangles in the aorta around the junction with the renal arteries. The other guide wire is fed in through the same leg and crosses over from one iliac artery into the other iliac artery and out through an incision in the common femoral artery of the other leg. See, for example, FIGS. 9 through 12, and the accompanying text of Baron et al., U.S. Pat. No. 5,360,443. The loose guide wire is used to guide the entire stent and graft assembly into the abdominal aorta above the iliac divide. The aortic or proximal end of the graft is exclusively fed through the femoral artery with the two iliac ends of the graft trailing behind. Thereafter, the second guide wire, which is looped up through both iliac ends of the graft, is used to help try to position the crossover iliac end into proper position in the iliac artery of the other leg. Beside the obvious difficulties in maneuvering the device, it is difficult to ensure that the graft does not become twisted and blocked during deployment. It is also difficult to control the placement of, in particular, the iliac portion of the graft which is being maneuvered into the non-insertion iliac artery.

Baron et al. also discloses insertion of an apparatus intraluminally to the aorta and in particular, to a ruptured aneurysm, through the axillary artery in the patients arm. See, for example FIGS. 13 and 14. However, this method and device appear limited to use in connection with ruptured aneurysms and Baron, et al. does not disclose the ability to accommodate a bifurcated graft.

Palmaz, et al., U.S. Pat. No. 5,316,022 disclosing inserting two individual grafts, rather than one bifurcated graft, through the individual femoral and iliac arteries up into the aorta. This leads to uniform sacrifice of the internal iliac circulation and would only be feasible in patients in whom both internal iliac arteries are already occluded. Also, the proximal end of the double individual graft stents will not, in all likelihood, produce a complete seal.

SUMMARY OF THE INVENTION

The present invention overcomes all of the disadvantages of the prior art by allowing for a simple, straight forward, surgical protocol which allows for complete control of the upper and lower ends of a bifurcated graft. In particular, the present invention allows the surgeon control of the graft from outside the body even while the graft is within the body. In some preferred embodiments, the present invention also allows a surgeon to dynamically adjust the length of the graft during surgery to provide for a perfect fit. The present invention further provides methods which can be primarily undertaken through the common femoral artery or through the supraclavicular subclavian artery.

The present invention accomplishes same by the use of surgical techniques which involve three incisions, one to allow access to each of the common femoral and iliac arteries and another to allow access to, in particular, the supraclavicular left subclavian artery. Other arteries such as, for example, the axillary arteries or the common carotids may also be used. Second, the present invention takes advantage of the use of uniquely designed delivery assemblies which allow for complete control of the placement of the graft.

In accordance with one aspect of the present invention there is provided a method of implanting an abdominal aortic graft into the body of a patient which includes a number of steps. First, access is provided through an access point or access port to the interior of the first and second iliac arteries of the patient. This can be done through an incision, puncture or the like. Similarly, access is provided through an access point to the interior of the abdominal aorta above the iliac divide and above the junction between the aorta and the renal arteries of the patient. Thereafter, a bifurcated graft having an abdominal end, a first iliac end and a second end is introduced into the abdominal aorta and the iliac arteries through one of the access points previously described. Finally, the graft is fixed into place such that blood can flow therethrough.

In one preferred aspect of the present invention, the bifurcated graft is delivered through the access point to the interior of the abdominal aorta above the iliac divide and above the junction between the aorta and the renal arteries. In a second aspect of the present invention the bifurcated graft can be introduced through the access point to the interior of one of the first or second iliac arteries of the patient.

In another preferred aspect of the present invention, the abdominal aortic surgical methods can include steps of stringing one or more guide wires through the patient's body. This can include stringing at least one guide wire through both the access point to the interior of the abdominal aorta and the access point to the interior of the first iliac artery such that both ends of the guide wire protrude from the body of the patient.

In accordance with another aspect of the present invention there is provided a method of implanting an abdominal aortic graft into the body of a patient which includes the step of providing access through an access point to the interior of the abdominal aorta above the iliac divide and above the junction of the aorta and the renal arteries of the patient as previously described. Thereafter, a bifurcated mandril assembly having an aortic end, a first iliac end and a second iliac end which includes a bifurcated graft is introduced into the abdominal aorta by inserting the first iliac end and the second iliac end of the mandril assembly into the abdominal aorta through the access point discussed above. This is accomplished before introducing the aortic end of the mandril assembly therethrough. The mandril assembly is then manipulated into place such that the first iliac end of the bifurcated mandril is disposed in the first iliac artery of the patient, the second iliac end of the bifurcated mandril is disposed in the second iliac artery of the patient and the aortic end of the mandril assembly is disposed in the abdominal aorta below the junction of the aorta and the renal arteries. Finally, the graft which is carried by the assembly is fixed in place. Thereafter, the mandril assembly can be withdrawn through the access point. In a particularly preferred embodiment of the present invention, the mandril assembly allows one to independently manipulate the first iliac end and the second iliac end, as well as the aortic end of the mandril assembly through the single access port.

Also in accordance with the present invention, there is provided a method of implanting an abdominal aortic graft in the body of a patient which includes the steps of providing access through an access point to the interior of the first and the second iliac arteries of the patient to the abdominal aorta therethrough. A bifurcated mandril assembly having an aortic end, a first iliac end and a second iliac end and including a bifurcated graft is then introduced into the first iliac artery by inserting the aortic end and the second iliac end of the mandril assembly into the first iliac artery before introducing the first iliac end of the mandril assembly into same. Thereafter, the bifurcated mandril is manipulated by manipulating at least the first and the second iliac ends of the mandril assembly into place in the first and second iliac arteries respectively. This can be done in such a way so as to position the aortic end of the mandril assembly in the abdominal aorta below the junction of the abdominal aorta and the renal arteries. This, in turn, means that the bifurcated graft is in the proper place for fixation. Finally, the graft is fixed in place.

One of the focuses of the methods of the present invention is that an aortic graft delivery system provides a surgeon with the ability to manipulate all ends of the bifurcated graft, dynamically, both before and after the graft enters the body. This allows the surgeon unmatched control over the movement and placement of the graft by directly manipulating each end of the graft through the vessel into which it will be delivered.

In one embodiment in accordance with the methods of the present invention, the supraclavicular left subclavian artery is used as the primary approach for delivery of the graft. In accordance with one embodiment of this method, a first and a second guide wire are inserted through the subclavian artery down into the abdominal aorta. Then one of each wires is run through each of the iliac arteries and out of the body of the patient through the common femoral arteries in the groin region of each leg. The first guide wire is then fed or threaded through the opening in the first iliac end of the graft and then fed through and out of the opening in the proximal or aortic end of the graft. The second guide wire is fed or threaded through the opening in the second iliac end of the graft and then out through the aortic end thereof. The graft can then be pushed and pulled into the abdominal aorta through the subclavian artery and moved into place exactly where desired. Because of the use of guide wires running into each of the iliac arteries and through each of the iliac ends of the graft, when the graft is advanced along the wires, it will naturally take up the necessary position in the aorta and in both of the iliac arteries. Moreover, because control over the top and bottom ends of the graft can be maintained at all times, simultaneously, the stents which are used to anchor the graft into place can be positioned exactly where desired.

In accordance with the present invention, it is possible to accomplish the foregoing with or without the use of guide wires. The former can be accomplished with the use of a bifurcated mandril as described in detail herein. The latter can be accomplished using a bifurcated mandril assembly for a bifurcated graft which, in essence, eliminates the need for the use of guide wires. For example, if the assembly were long enough, its iliac ends (those carrying the iliac ends of the bifurcated graft) could be inserted directly into the subclavian artery, down into the aorta and into each of the iliac arteries and then pulled out of the body through the common femoral arteries in each leg. The graft could remain out of the body even while the lower ends of the assembly protrude from the common femoral arteries. This would also allow a surgeon to control the exact placement of the graft by allowing the graft to be pushed and pulled into proper position by manipulating the three ends of the assembly alone. Hybrid devices are also contemplated which include built-in guide wires. Also, the graft and mandril assembly could be coupled to a guide wire such that pulling on the guide wire will assist in placement of the graft.

In another embodiment in accordance with the methods of the present invention, the same three incisions are made. However, instead of delivering the graft into the aorta and the iliac arteries via the abdominal aorta above the iliac divide, the graft will be inserted through the iliac arteries via the common femoral arteries. In this instance, only one guide wire is fed from the subclavian out through one of the femoral arteries. A second cross-over wire is fed from the femoral artery through which the first guide wire is threaded, up through and over the divide of the aorta into the iliac arteries and back again out through the common femoral artery in the other leg, the non-insertion leg.

Instead of feeding the proximal end of the graft up into the aorta and then trying to manipulate the cross-over portion of the graft into appropriate placement in the iliac artery as is done in the prior art, the aortic end, and the cross-over iliac portions, or second iliac end of the graft which are disposed on a bifurcated mandril assembly are both fed into the first femoral artery then into the first iliac artery and finally up into the aorta and second iliac artery by pushing and pulling the graft and the assembly, the first iliac end of the assembly is thereby carried into the first iliac artery. In so doing, the upper end of the graft is naturally manipulated into a position below the renal arteries. Also, the cross-over leg or second iliac end of the graft follows the cross-over guide wire directly into place in the non-insertion or second iliac artery. Because control is maintained over each end of the graft during insertion, it is possible to insure the correct placement of the graft and its stents.

Again, the invention has been described in terms of a method and apparatus utilizing guide wires. However, it is possible through the use of a very long mandril, to insert a mandril into the common femoral artery, through the iliac artery, into the aorta and out through the subclavian artery. The other portion of the mandril carrying the crossover end of the graft can be fed up and brought around the aortic bifurcation and out through the common femoral artery of the other leg. By manipulation of these mandrils, it is possible to pull the graft into its proper orientation and ensure proper deployment of the same. Hybrid devices which use a first guide wire running between the subclavian and the first iliac arteries and an extended mandril (without a guide wire) may be used for the crossover leg.

Through the use of either aspect of the present invention, it is possible to obtain a previously unknown degree of control over the placement of a bifurcated graft, in terms of insuring that both the aortic and the iliac portions of the graft are appropriately placed. The present invention also ensures that the ends of the graft are fixed in the appropriate places. Placement of the graft is nearly mistake proof. Finally, as explained in more detail herein, some of these methods and devices allow the surgeon to adjust the exact length of the graft to insure proper fit, during surgery. The methods in accordance with the present invention can accommodate both self-expanding and balloon expandable stent based devices.

While the previous methods and devices described have all utilized both an incision or access point to the abdominal aorta disposed above the iliac divide and above the junction between the abdominal aorta and the renal arteries as well as access points or incisions in both legs of the patient to provide access to the common femoral arteries and more particularly the iliac arteries, the present invention is not limited thereto. For example, in accordance with one aspect of the present invention, a single incision can be made in the subclavian and a bifurcated mandril including a bifurcated graft may be fed through the subclavian access down into the abdominal aorta and the iliac arteries. More preferably, the device used will allow for some measure of control over the distal ends of the bifurcated mandril and graft to assist in ensuring that the first and second iliac ends of the graft are properly placed in the respective iliac arteries. This can be accomplished through the use of guide wires (including guides wires which do not protrude through the groin of the patient) and/or the use of an iliac stent containing mandril whose position can be influenced while inside the body. For example, the iliac ends of the mandril can be combined with tips which are essentially moveable and curved so as to influence the steering of the mandril or the iliac ends of the mandril can include, for example, flotation catheters.

Similarly, it is possible to insert a bifurcated graft using a bifurcated mandril which is inserted through one of the iliac arteries without providing access to the abdominal aorta through an incision or access point disposed above the iliac divide and the junction between the abdominal aorta and the renal arteries. Because of the methods and devices of the present invention, the difficulties normally associated with the accurate deployment of the iliac ends of a graft are still overcome. Moreover, these prior art recognized difficulties are overcome in a way which allows the surgeon to maintain sufficient control over the aortic stent, if not direct control so as to render surgical procedures relating to same practicable.

Because of the advantages of the surgical methods and devices described herein, and the use of blood vessels at both ends of the torso, unmatched control of both ends of the graft is provided to the operating surgeon. Therefore, the surgeon is able to insure proper placement of the graft. The invention also allows for the use of lighter gauge, more flexible guide wires and in some cases, the elimination of guide wires altogether. This in turn allows for the use of smaller and smaller graft delivery devices minimizing stress to the vessels during surgery. In addition, lower profile devices make access options more easily available. Moreover, the resulting increase in flexibility allows for negotiating various turns in blood vessels. Thus, other blood vessels may be used as introduction points. Of course, ultimately, percutaneous access is the goal. The ability to control the graft, coupled with its small size and great flexibility minimizes contact between the prosthesis and the vessel wall during insertion thereby reducing the likelihood of plaque or thrombus dislodgment. Because of the ease of surgery using the present invention, operating time is reduced as is the cost of performing application. The need for further surgery due to a graft which is improperly sized or deployed can also be virtually eliminated.

7

FIG. 9 illustrates the final placement of a bifurcated mandril in accordance with the present invention in the area of aneurysm.

FIG. 10 illustrates the deployment of the aortic stent.

FIG. 11 illustrates a bifurcated mandril for delivering a bifurcated graft including balloon expandable stents.

FIG. 12 is a view of the bifurcated mandril of FIG. 11 illustrating the expansion of balloons and the expansion of a balloon expandable stent.

Figure 13:
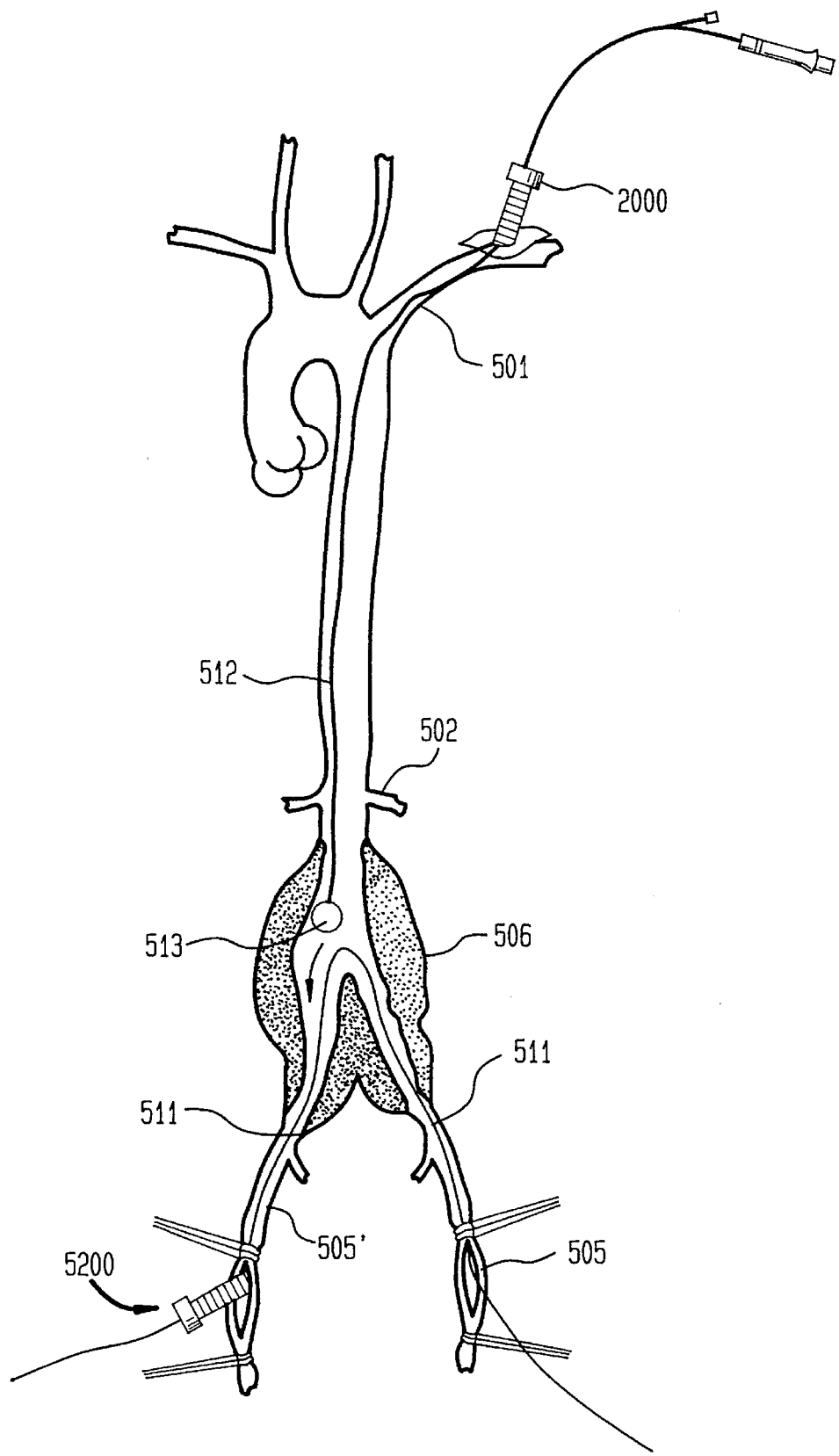

FIG. 13 illustrates another preferred embodiment of threading guide wires for a distal mandril assembly.

Figure 14:
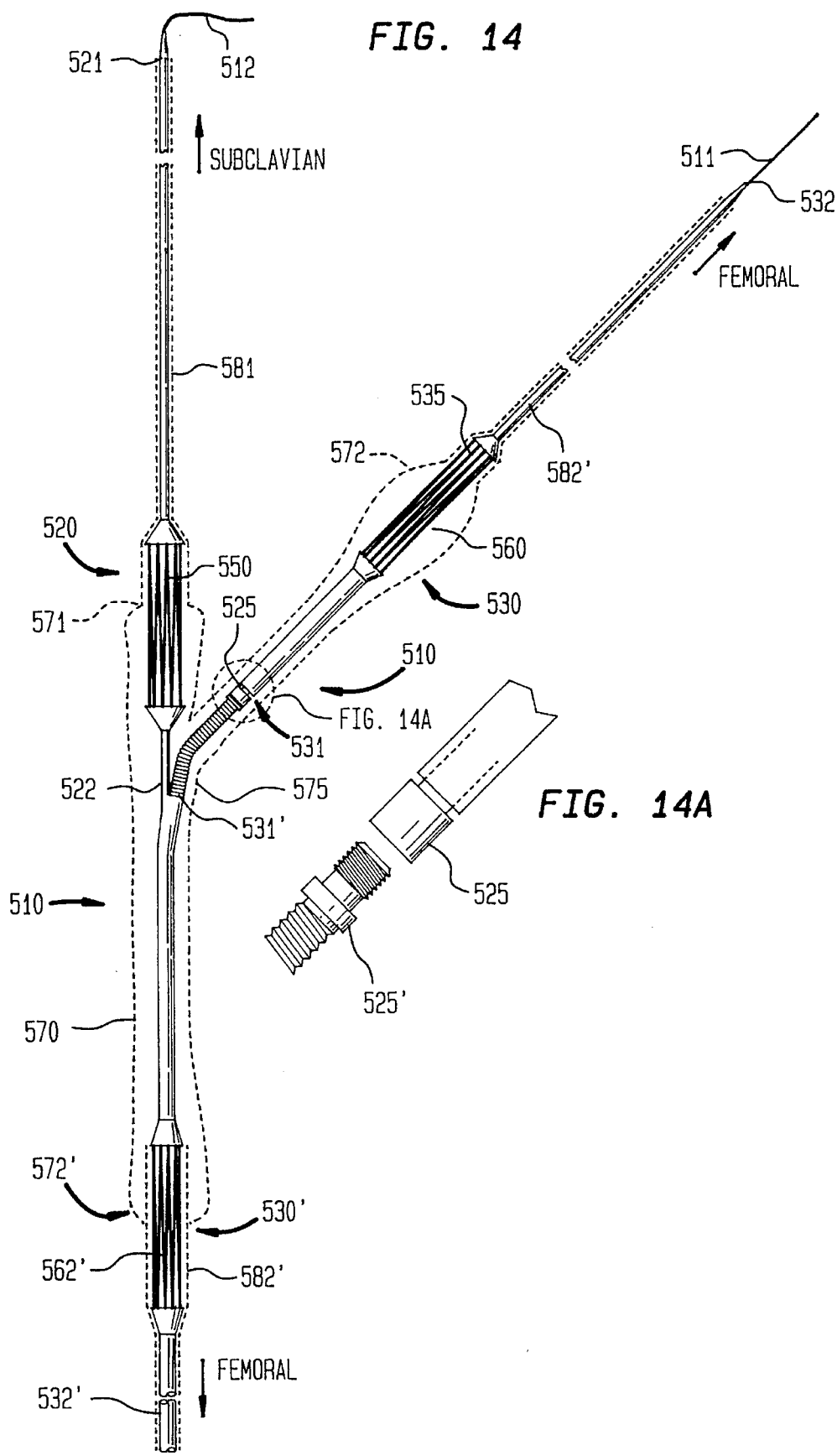

FIG. 14 illustrates a bifurcated mandril assembly for a distal insertion application having self-expandable stents.

FIG. 14a is an exploded view illustrating the coupling member and bridge components of the bifurcated mandril assembly of FIG. 14.

Figure 15:
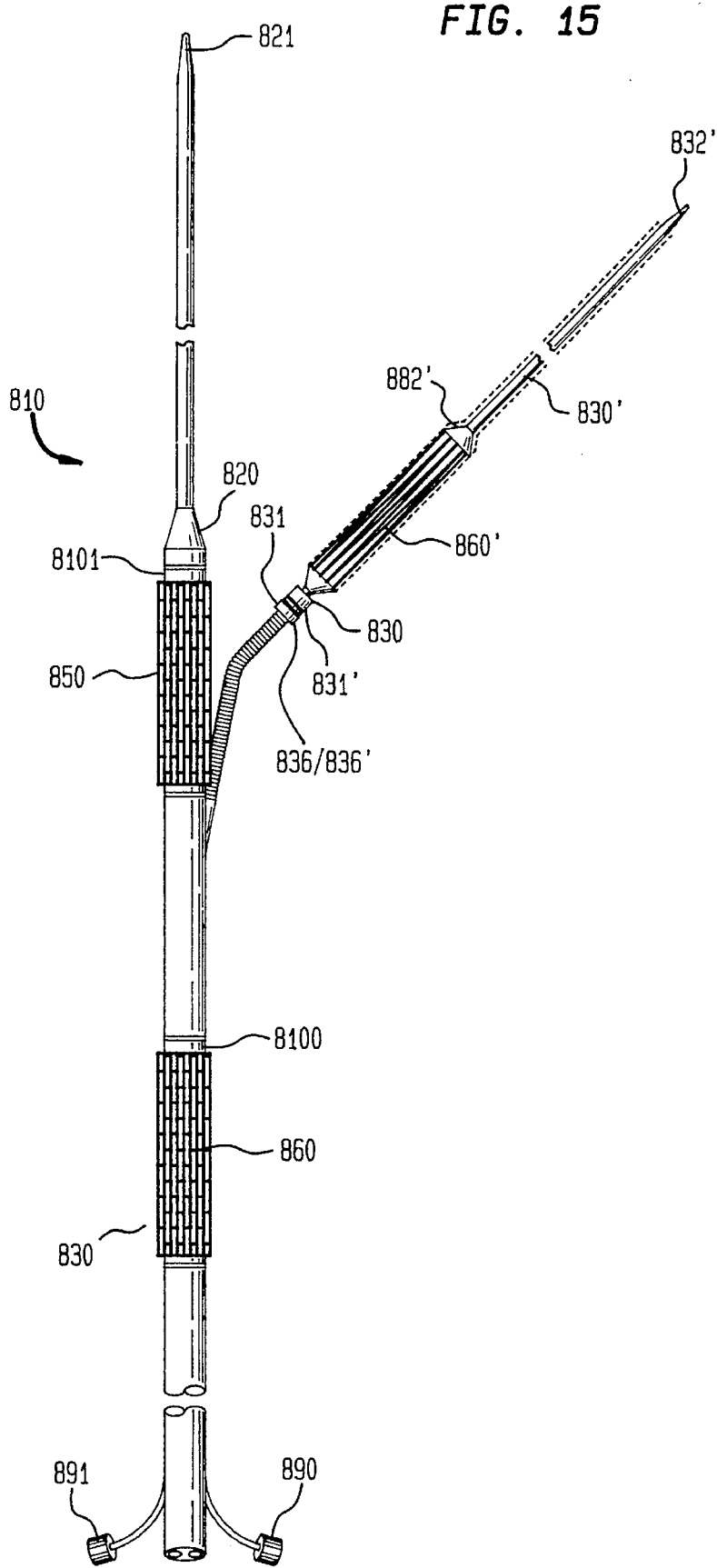

FIG. 15 illustrates a bifurcated mandril for a distal insertion method including both self-expandable and balloon expandable stents.

FIG. 16 is an illustration of a self-expanding stent.

Figure 17:
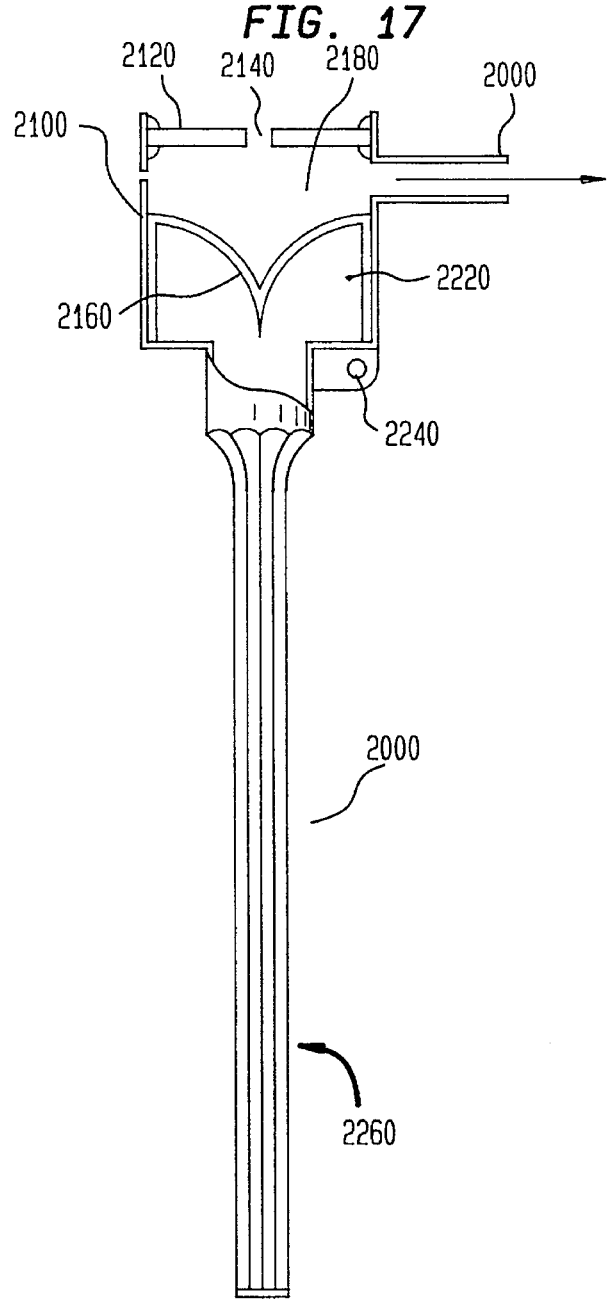

FIG. 17 is a view, in partial cross-section, of a balloon expandable universal access sheath.

Figure 18:
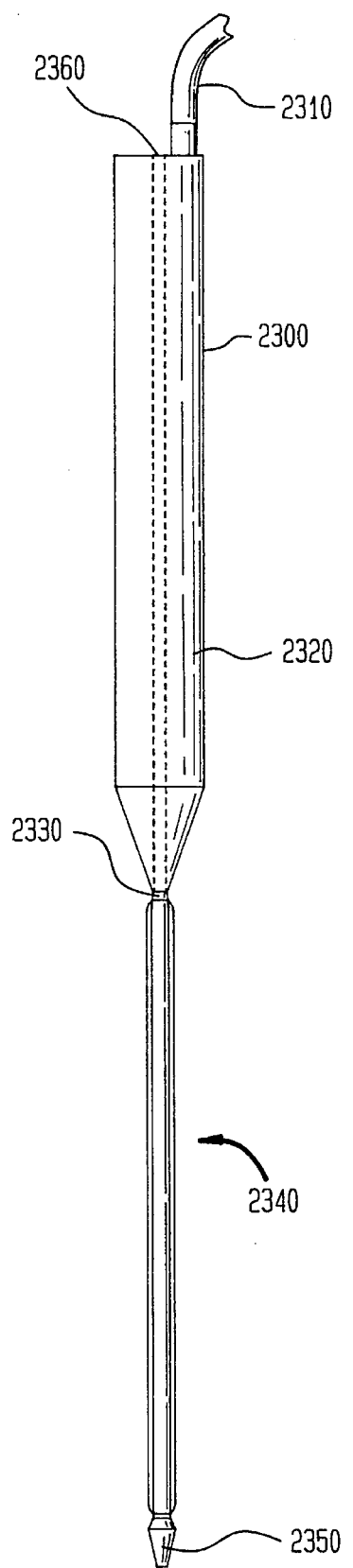

FIG. 18 is a view, in partial cross-section, of a balloon inflation device for use in conjunction with a balloon expandable access sheath.

Figure 19:
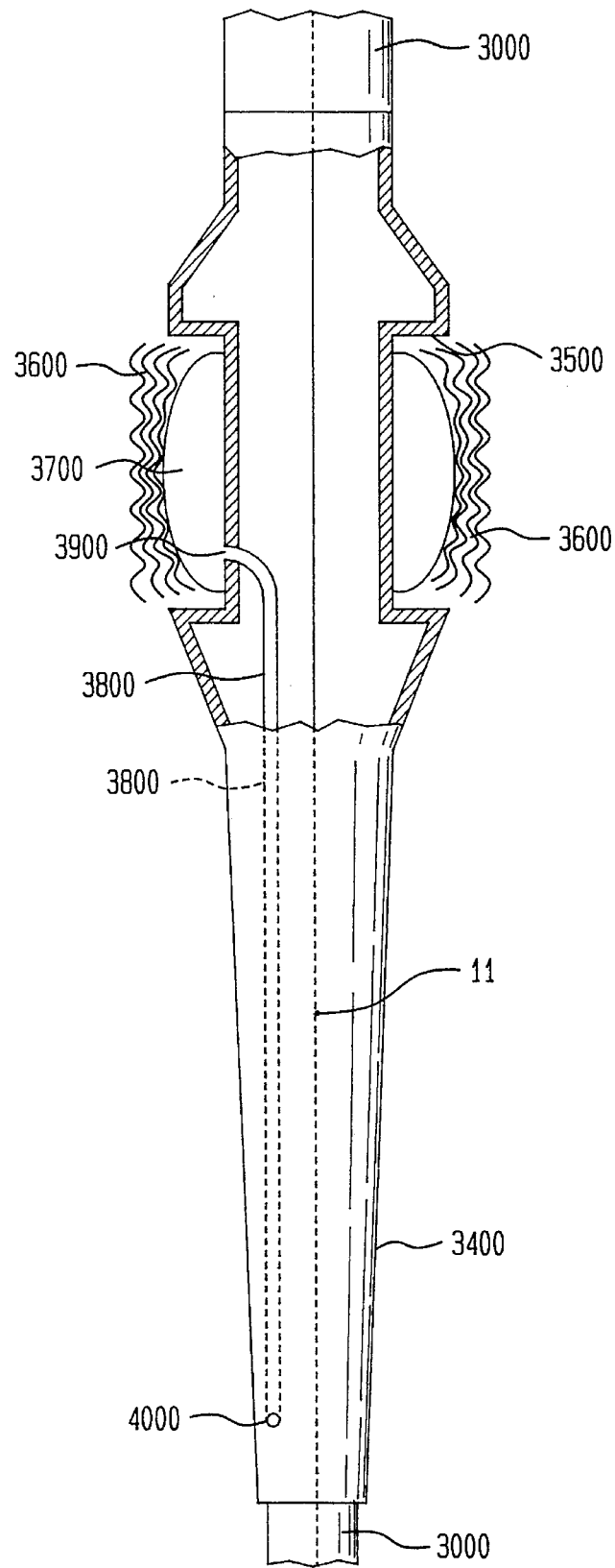

FIG. 19 is a illustration, in partial cross-section, of a distal mandril including an inflation balloon disposed beneath a self expanding stent which can be inflated from outside of the body of the patient.

DETAILED DESCRIPTION OF THE PREFERRED EMBODIMENT

Figure 1:
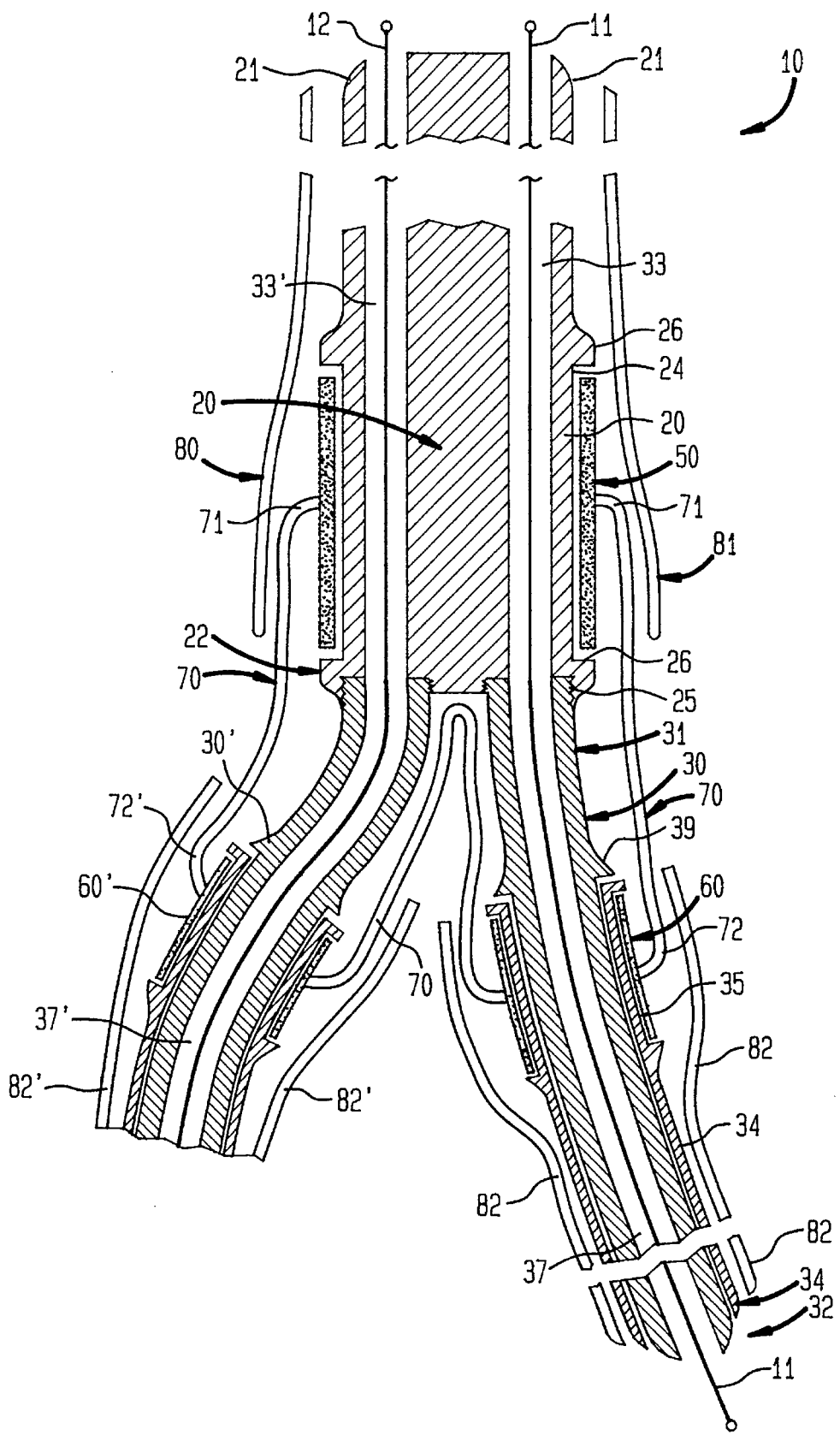
FIG. 1 is a cross-sectional view of a bifurcated mandril assembly in accordance with the present invention including a bifurcated graft which is retained by a plurality of sheaths.

In accordance with one preferred embodiment of the present invention, a graft carrying assembly is used to carry a bifurcated graft to an aneurysm. FIG. 1, which along with the other figures is not to scale, illustrates one graft carrying mandril assembly 10 in accordance with the present invention.

Assembly 10 is intended for insertion into a patient, and the elements of assembly 10 are generally described as being "proximal" or "distal" depending on their relative position with respect to the head and feet of the patient. When a member is referred to as having a "proximal" or "upper" portion and a "distal" or "lower" portion, the "proximal" or "upper" portion shall generally refer to the portion closest to patient's head and the "distal" or "lower" portion shall generally refer to the portion closest to the patient's feet. Referring to elements as being "proximal", "distal", etc. is for ease of reference purposes only, and should not be construed as requiring a specific location or direction with respect to the position of the patient's body.

Assembly 10 includes upper mandril 20, and two lower mandrils 30, 30'. Upper mandril 20 is generally cylindrical, and extends from a proximal end 21 to a distal end 22. The upper mandril also has two channels 33, 33' extending from the proximal end to the distal end, and the channels are sufficiently large enough to accept guide wires 11, 12 respectively. Although not shown, a single channel large enough to accommodate both wires may also be used. The upper mandril 20 also has a recess 24 which extends around the outer surface of the mandril. The recess holds a cylindrical self-actuating or self expandable aortic stent 50, and the edges 26 of recess 24 prevent the axial movement of the stent, i.e. movement parallel to the longitudinal axis of the mandril.

At the distal end 22 of mandril 20 are means 25 for detachably coupling lower mandril 30 to upper mandril 20. In the preferred embodiment of FIG. 1, coupling means 25 comprises screw threads on the outer surface of the proximal end 31 of lower mandril 30, and cooperating threads in channel 33 at the distal end 22 of upper mandril 20. However, any arrangement which can allow for the detachable coupling of the upper mandril 20 and lower mandril 30 is structurally acceptable. For example, detachable coupling means 25 may also include a different threaded assembly, a detachable pressure coupling, a slidable coupling member, a series of perforations, or other similar means.

Lower mandril 30 also includes a hollow channel 37 extending from its proximal end 31 to distal end 32. Lower mandril 30 is generally cylindrical, but preferably narrower in diameter than upper mandril 20. Channel 37 is cooperatively disposed relative to channel 33 of the upper mandril such that upon exiting channel 33 of upper mandril 20, guide wire 11 passes into and through channel 37. A housing 34 is disposed on the outer surface of the lower mandril, and extends from raised edge 39 below the proximal end 31 until near the distal end 32. Housing 34 is preferably fixed in place such that it is not capable of axial movement with respect to the length of mandril 30, but is freely rotatable about the mandril's longitudinal axis. In other words, the housing 30 cannot move up and down the mandril, but can rotate about it. Housing 30 also defines a recess 35 on its outer surface for holding a self-actuating or self expanding cylindrical iliac stent 60.

Another lower mandril 30' is also detachably engaged with the distal end 22 of the upper mandril. Lower mandril 30' has the same structure as lower mandril 30, including a channel for accepting guide wire 12, and a rotatable housing with a recess for holding an iliac stent 60'.

Figure 2:
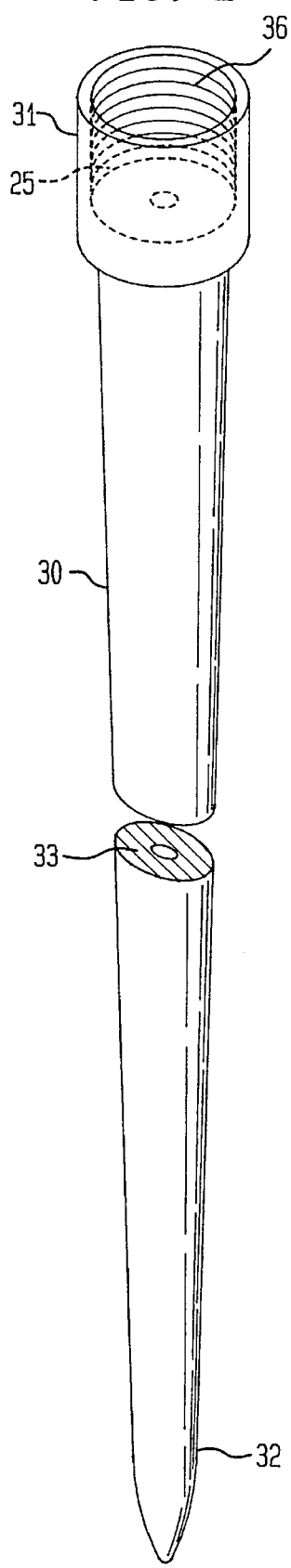
FIG. 2 is a view of a threaded lower or iliac mandril assembly.
Figure 3:
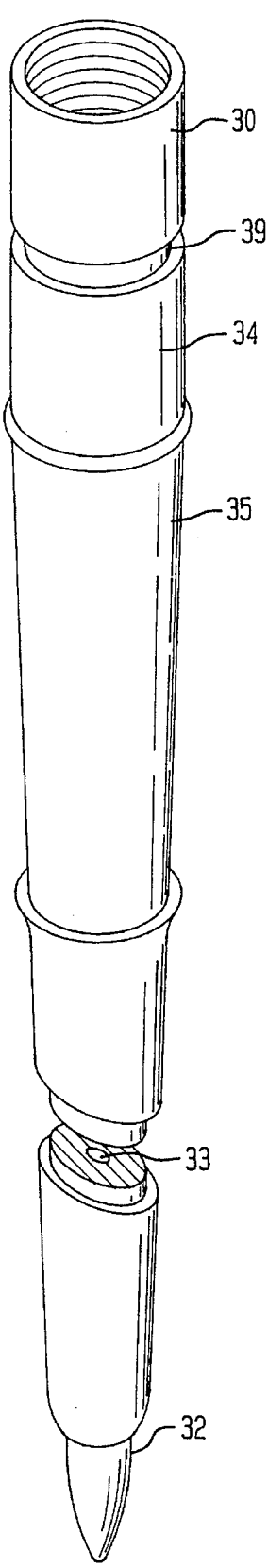
FIG. 3 is a view of the mandril assembly of FIG. 2 further comprising a housing and a recess for retaining a stent.
Figure 4:
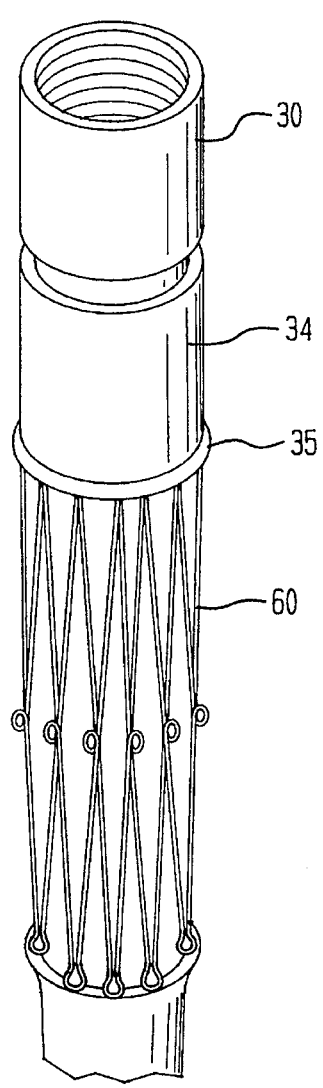
FIG. 4 is a view of the mandril of FIG. 3 further illustrating a self-expanding stent.

FIGS. 2–4 offer a perspective view of alternative lower mandrils with a somewhat different coupling structure than the lower mandril shown in FIG. 1. FIG. 2 shows a mandril 30 with channel 33 through which a guide wire may be passed. However, FIG. 2 also shows an alternative coupling means 25 whereby the threaded receiving member of the lower mandril has a wider inside diameter than the corresponding threaded member at distal end 22 of upper mandril 20. FIG. 3 illustrates the same alternative lower mandril 30 but contained in housing member 34. The housing member 34 starts at raised edge 39 and ends at or near the distal end 32 and is freely rotatable around mandril 30. As shown in FIG. 4, iliac stent 60 is disposed and retained in recess 35.

The actual distance between the proximal ends and distal ends of the various mandrils or members are preferably quite large compared to the mandrils' diameter. For example, the length of upper mandril 20 may be 100 cm while the diameter is 5 mm. All of the mandrils should be of a material sufficiently flexible for being threaded through the arteries of a patient, such as hollow, helically coiled wire or molded plastic.

As shown in FIG. 1, a bifurcated graft 70 is attached to stents 50, 60, and 60'. The graft is pant-shaped or "Y" shaped having an open proximal or aortic end 71 and two open distal or iliac ends 72, 72'. Proximal end 71 is preferably attached midway between the ends of aortic stent 50 in nearly any manner known in the art. Preferably, the graft is sutured to the stents, using for example, interrupted, non-absorbable sutures. Each distal end 72, 72' of the graft 70 is attached midway between the ends of the corresponding iliac stents 60,60' of lower mandrils 30,31'. In other words, the Y-shaped graft 70 is fitted over assembly 10 at the junction between the upper mandril and the lower mandrils and is attached at its ends to the middle of the stents.

A wide variety of stents are known and can be used. In such cases, the graft 70 may not be attached to the stents in the manner just described. Rather, attachment will be dictated by the stent itself.

A number of commercially available bifurcated grafts 70 may be used. For example, the Bard Velex graft available from C. R. Bard, Inc. may be used. A thinner version of such a graft could also be used as the graft is being used endo-luminally i.e. inserted within an already existing vessel. Also, an expandable PTFE graft manufactured by Impra of Scottsdale, Ariz. may be used. When PTFE is used, and, in particular, where an adjustable length graft will be used, the graft must be designed to accommodate stretching. Preferably, graft 70 is adjustable in terms of length. Specifically, the iliac and/or aortic portion of the graft may be constructed using accordion-type folds or pleats (crimped) which, when pulled, will expand allowing for the adjustment of the length of the graft and, in particular, the placement of the iliac stents. The actual size of the graft is chosen by the surgeon based on the particular needs of the patient. For example, a 16×8 graft 70 will have a 16 millimeter opening at upper end 71 and 8 millimeter openings at distal ends 72,72'. The graft 70 itself is made of a flexible material which may stretch to accommodate vessel growth, and/or to allow the graft to be used over a wide range of lengths.

The assembly 10, including the graft 70, is then encased in a removable sheath. The sheath may be a single integral unit, but is preferably three separate sheaths 81,82,82', covering the stents on the upper mandril and the lower mandrils, respectively. Sheath 81 extends from approximately the proximal end 21 of upper mandril 20 to the distal end 22. Likewise, sheaths 82,82' extend from approximately the proximal ends of lower mandrils 30,30' to the distal ends of the lower mandrils. The sheaths are sized to tightly fit over the mandrils, stents and graft to prevent the stents from expanding.

In operation, the device just described may be used as follows. First, the patient is prepped from neck to knees and draped in a fashion to expose the left of the neck above the clavicle and both groins. The patient is laid supine with the neck hyper-extended and turned to the right. General or local anesthetic, the latter with a sedative, may be administered.

Figure 7:
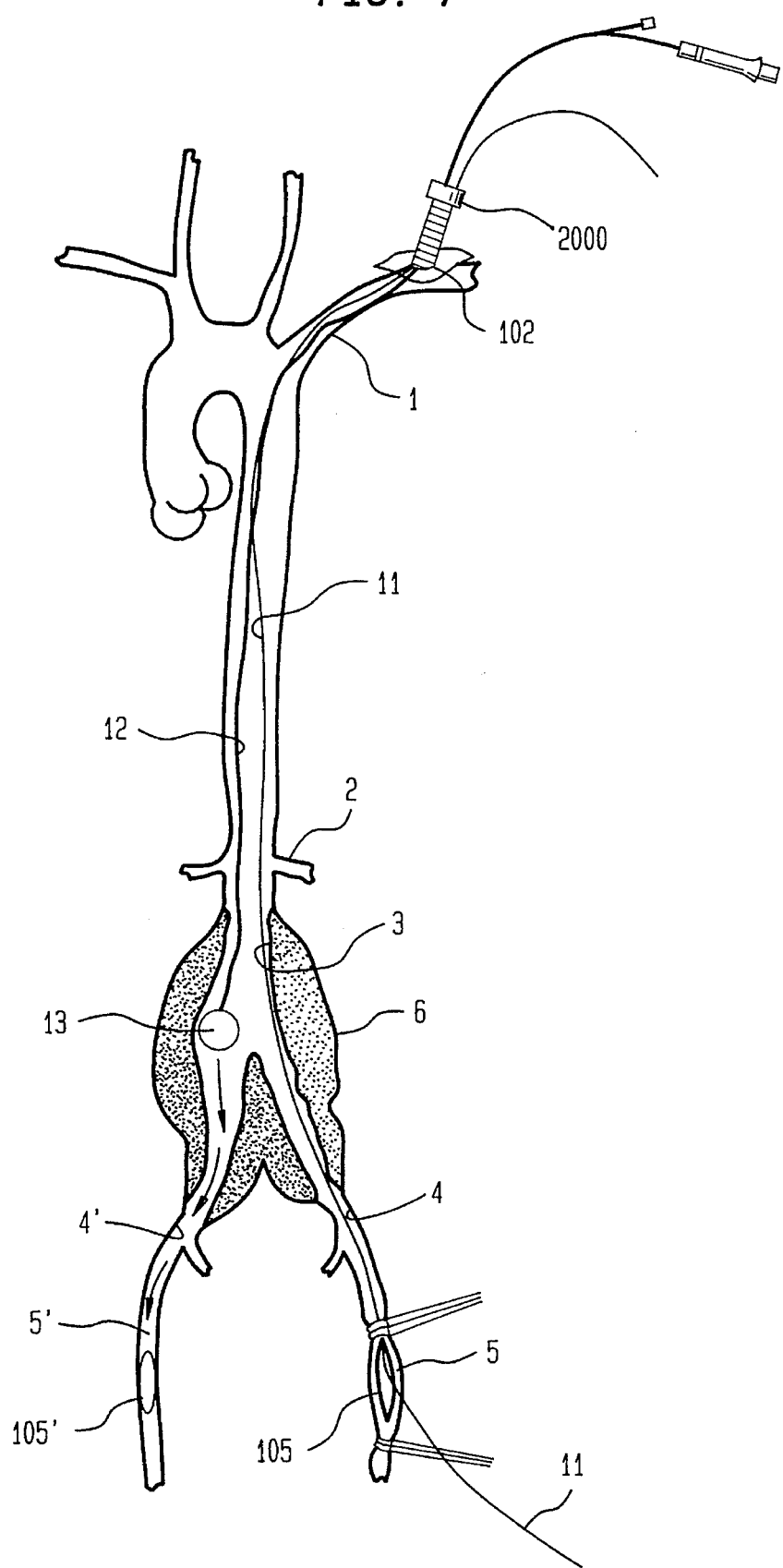
FIG. 7 is a view of an aneurysmal aorta illustrating the insertion of guide wires through a balloon expandable universal access sheath.
Figure 8:
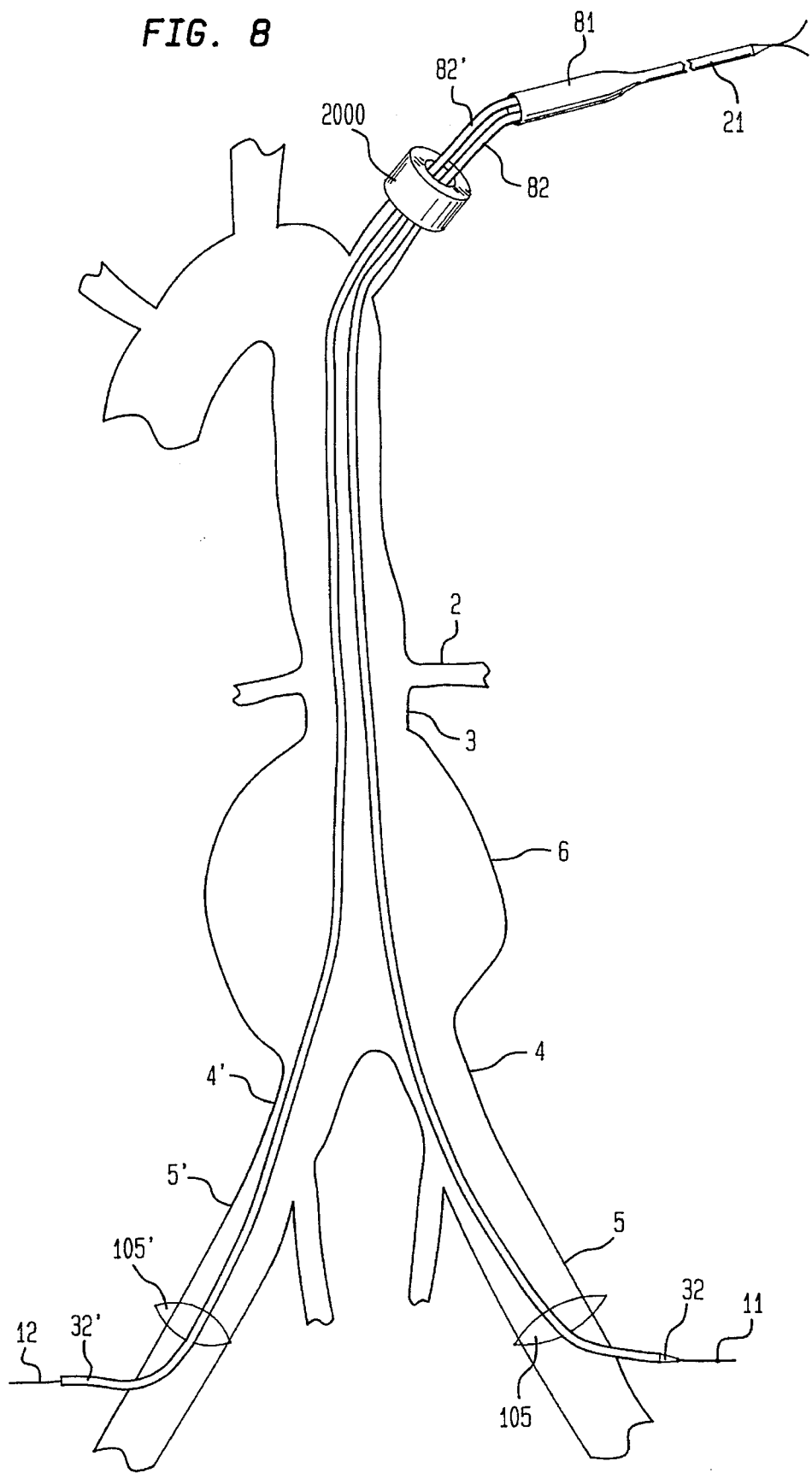
FIG. 8 illustrates the insertion of a bifurcated mandril assembly over guide wires.

As shown in FIGS. 7 and 8, a transverse skin incision is made above the left clavicle and the lateral third of the left sternocleidomastoid muscle is divided and retracted medially. The internal jugular vein also retracted medially exposing the scalenus anticus muscle. The phrenic nerve runs along the antero-lateral border of the scalenus anticus muscle and injury must be avoided during the procedure. The scalenus anticus muscle is then divided to expose the subclavian artery 1 (and specifically, the supraclavicular left subclavian artery). The subclavian artery 1 is encircled and mobilized circumferentially, taking care not to enter the pleural cavity. The branches of the subclavian artery are controlled with loops of 2–0 silk.

Longitudinal incisions are then made in both femoral regions. The common femorals 5,5', the superficial femoral and the profounda femoris arteries in both groin regions are isolated and controlled with vessel loops. The common femoral arteries 5,5' are mobilized circumferentially as high as possible into the region of the iliac arteries 4,4' and any tortuosity is straightened out by this dissection.

As illustrated in FIGS. 7 and 8, a puncture is made into the subclavian 1 and a Balloon Expandable Universal Access Sheath ("BEUAS") 2000 or some other, conventional, access port is inserted (the BEUAS 2000 is illustrated in FIGS. 17 and 18). A large bolus of Heparin is given. A first guide wire 11 is then inserted through the BEUAS. Although the guide wire may be guided through the body with a guide catheter, the wire is preferably passed within a floatation catheter 13. The use of a flotation catheter takes advantage of blood flow for placement and minimizes the contact between the guide wire and the arterier wall. Guide wire 11 is fed down through subclavian 1, past renal arteries 2, through the abdominal aorta 3 and past the aneurysm 6 to be treated, into and through iliac artery 4, and finally out a small transverse arteriotomy 105 made in the common femoral artery 5 of the patient's leg. Likewise, a second guide wire 12 is fed into the subclavian 1 and out another incision 105' in the common femoral artery 5' of the other leg.

Thus, the free ends of both guide wires 11, 12 protrude from the patient's body, one end of each wire protruding from each leg and the other ends both protruding from the subclavian. Sufficient wire 11, 12 is left protruding from the body to allow for easy manipulation. The guide wires 11, 12 may be as much as 12 feet in length, or even longer. Specifically, the guide wire should be sufficiently long to allow for control of both ends to be maintained, even when the graft is put into place. As will be self-evident, once the graft is in position in the aorta, for example, its distal mandrils will extend from the patient a considerable number of feet. Therefore, to maintain firm control over the system, the guide wire must be sufficiently long to accommodate and allow access thereto even when the full length of the mandril is exposed through the patient's legs.

The portions of wires 11,12 extending out of subclavian 1 are then fed into and through the appropriate channels 37, 37' of the lower mandrils and then channels 33, 33' of the upper mandril. (see FIG. 1). Once the assembly 10 has been placed on the guide wires, the two distal ends 32,32' of the sheathed assembly 10 are inserted into the subclavian 1 through the BEUAS 2000 and fed through the patient's body until the ends 32,32' protrude from the incisions in the common femoral arteries 5,5' (FIGS. 8–9). Alternatively, the assembly can be releasably attached to the guide wires 11, 12 such that the assembly can be pulled into place by pulling on the guide wires. This can be accomplished by some type of stop placed on the guide wires above the assembly 10 threaded thereon which will engage the proximal end 20 of the assembly 10. When the wires 11, 12 are pulled through the femoral arteries 5, 5', the stops will engage the assembly 10 and pull it into place.

As soon as the ends of the mandrils protrude from the body, the graft 70 is ready to be introduced into the body and positioned. Graft 70 in combination with the mandril assembly 10 are advanced along guide wires 11,12 and moved to aneurysm 6 by manipulating the protruding portions of the mandrils, i.e. by pulling and pushing on lower ends 32, 32' and upper end 21 (FIG. 9). While feeding the graft through the patient, care must be taken to ensure the sheaths 81, 82, 82' remain in place in order to prevent premature deployment of the stents.

The graft is correctly positioned within the aneurysm 6 when the aortic stent 50 is in position below the junction with the renal arteries 2 (FIG. 9). When the graft is finally positioned, the graft and stents will be completely within the patient's body, while portions of the guide wires 11, 12, mandrils 20, 30, 30', housing 34, 34' and sheaths 81, 82, 82' will all extend out of the patient. The position of the graft 70 can be confirmed by reference to an anglogram which is taken using a pigtail catheter and an operating table having a radio-opaque ruler at the beginning of the procedure.

The graft is deployed by removing the individual sheaths. Once aortic end 71 of the graft 70 is in position, the aortic stent 50 is deployed by removing the sheath 81 by pulling the sheath back through the subclavian artery 1 (FIG. 10). Although the sheath 81 is tightly disposed around the graft 70 and upper mandril 20, it is not so tight that it can not be pulled off the upper mandril, especially when the lower mandrils 30 are held in place. As shown in FIG. 10, once the sheath 81 is pulled off graft 70, the self-actuating stent 50 will expand out of recess 24 and push the proximal end 71 of the graft against the walls of the aorta 3 above the aneurysm 6. This fixes the upper end 71 of the graft 70 into place in the aorta 3.

Next, the lower mandrils 30 are detached from the upper mandril 20. For example, in accordance with the preferred embodiment shown in FIG. 1, the upper end 21 of the upper mandril 20 and the housing 34 of the lower mandril 30 are grasped and prevented from rotating. Next, lower mandril 30 is rotated by rotating the lower end 32. By rotating lower mandril 30 while upper mandril 20 is kept in place, the screw coupling 25 will come undone and the lower mandril will be detached from the upper mandril. Further, because housing 34 is prevented from rotating, the lower mandril 30 will be able to spin within housing 34 without twisting the iliac leg of the graft 70, stent 60 or sheath 82.

Once the lower mandril 30 is detached from the upper mandril assembly, the lower mandril is manipulated to a position such that the lower end 72 of graft 70 is the correct position within iliac artery 4. In other words, the graft 70 is pulled and stretched to the appropriate length. Once in position, the housings 34 and mandril 30 are kept steady while sheath 82 is retracted through the common femoral artery, thereby deploying the iliac stent 60 and fixing the distal end 72 of graft 70 in place in iliac artery 4. For accuracy and simplicity, usually the two legs are done sequentially. For example, the other iliac stent is deployed in the other leg in the same manner described in connection with the foregoing stent.

It may also be desirable to include within those portions of the distal and proximal mandrils which remain exposed from the patient's body, a structure which helps prevent the premature deployment of stents 50, 60, 60' by inadvertent removal of sheaths 81, 82 and 82. This can be accomplished by the use of a collapsible structure at each end of the mandril assembly which will protrude from the patients body. The structure stretches the sheath in the localized area thereof making it difficult to move the sheath axially relative to the housing, mandril and/or other structures. Therefore, the surgeon can grip the entire assembly, including the sheath, between that structure and the outer-most end of the mandril, without significant fear of inadvertently deploying the stent covered by that sheath. If, as preferred, the sheath is made of a more rigid, slick, plastic material, then the assembly can be gripped above this structure without fear of inadvertent stent deployment as well. To deploy the stent either the sheath can be gripped above this structure and/or the device can be compressed or collapsed such that it no longer provides additional resistance. The structure could be a retaining band, a collapsible balloon, a spring loaded bearing or pad, a hook or latch, and the like.

Following the deployment of the right and left iliac portions of the graft 70, the various portions of the lower mandrils 30, 30' and housings 34, 34' are withdrawn through the femoral incisions and the upper mandril 20 is removed through the subclavian artery. Following the surgical procedures, a pigtail catheter is once again inserted into the surgical region to give a completion arteriogram. The guide wires 11, 12 are also removed. If satisfactory, each leg is flushed and femoral blood flow is restored after the arteriotomics are closed. The incisions are then closed and the wounds dressed.

A variety of advantageous alternatives to the preferred embodiment described above are also possible. In the preferred embodiment above, the housing 34 was allowed to freely rotate relative to the lower mandril 30 in order to allow the mandril 30 to be unscrewed without effecting the position of the housing 34 and, therefore, causing a twisting of the graft 70. If some other form of detachment means is used, it may not be necessary to include an independently rotatable housing 34. For example, if the lower mandrils 30, 30' are connected to the upper mandril 20 by a microperforation or by some form of pressure or snap coupling, then it may be possible to build the housing 34 and/or the recess 35 into the mandril 30 per se.

In addition, guide wires 11, 12 could be eliminated by designing systems such that mandrils 20 and, 30 are sufficiently long, sufficiently rigid, and sufficiently tapered so as to allow insertion directly through the subclavian 1 down into the aorta 3, through the iliac arteries 4 and out through the femoral arteries 5. In other words, rather than guiding the assembly through the body on a track of guide wires, long wiry mandrils themselves are used. Otherwise, however, the device can remain substantially unchanged. Such a system may be smaller than the embodiment shown in FIG. 1 by eliminating channels 33, 33', 37, 37'. A small upper mandril diameter may help reduce surgical trauma.

It is also possible to construct a hybrid device where a guide wire is permanently embedded in the mandril to provide a sufficient degree of rigidity and flexibility to allow the mandril to be properly placed with as little stress as possible upon the blood vessels.

Figure 5:
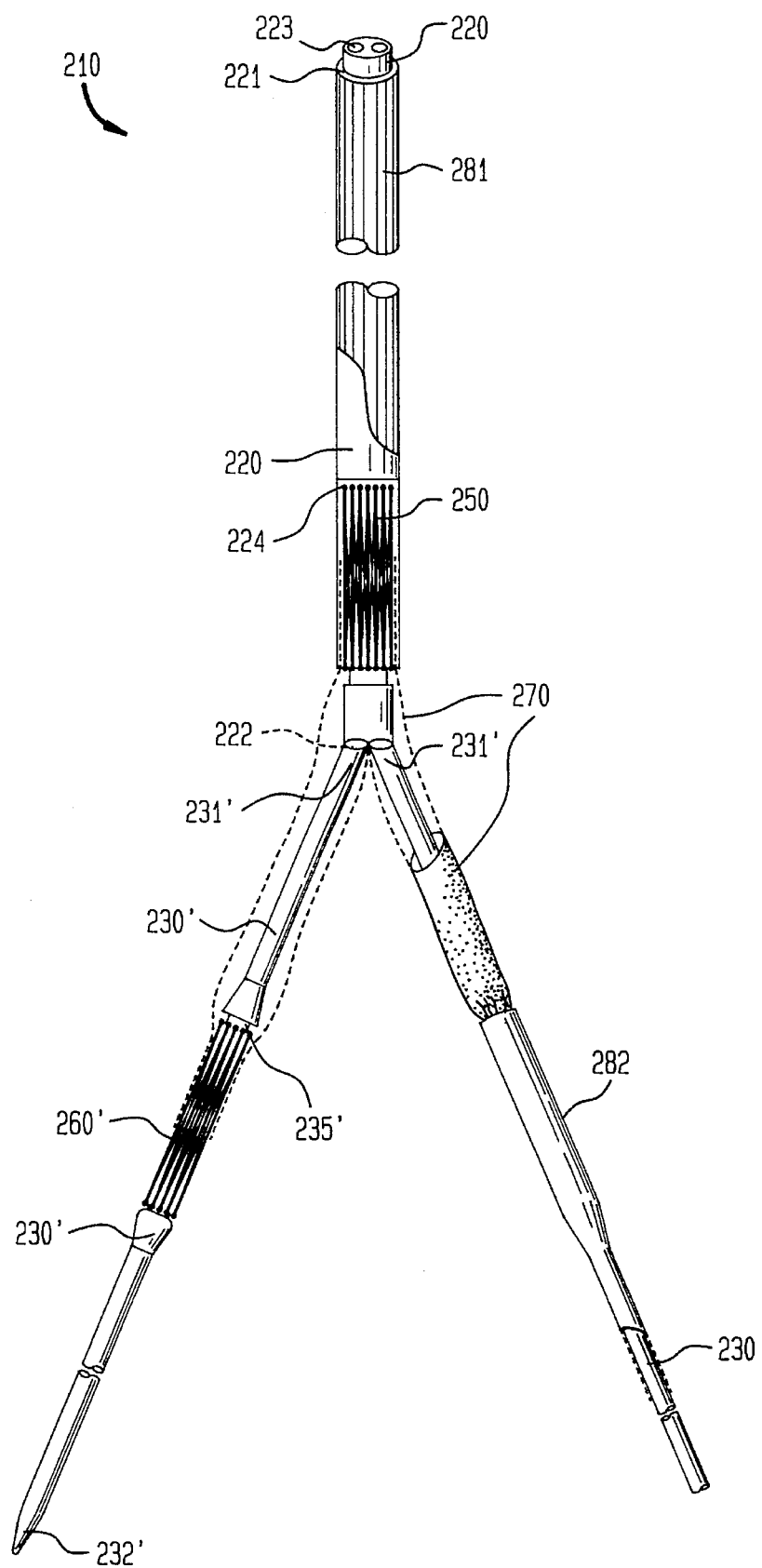
FIG. 5 is a partial cross-section of a mandril assembly, graft and sheath for a fixed length graft.

The above-described assembly 10 of FIG. 1 may be used with either fixed or variable sized grafts. FIG. 5 illustrates another embodiment using an assembly which is particularly adapted for introducing grafts of a fixed length. Because it is not necessary to stretch a fixed-size graft, lower mandrils 230, 230' are permanently attached to and/or integral with the distal portion 222 of the upper mandril 220. In this embodiment, as in any embodiment which utilizes distal or lower mandrils 230, 230' which do not need to be rotated for removal, it is possible to eliminate the use of housing members 34, 34' by building recess 235' directly into the lower mandrils to retain the iliac stent 260'. When the sheaths 281, 282, 282' are withdrawn such that the aortic stent 250 and iliac stents 260 are deployed, the entire assembly including the upper and lower mandrils can be withdrawn through the subclavian 1 incision.

As shown in FIGS. 11–12, this latter design of non-detachable lower mandrils is particularly useful in combination with balloon expandable stents. In the case of balloon expandable stents, an air or gas inlet 390, 391, 391' is built into the proximal end of the assembly 310, and these inlets communicate with balloons 300, 301, 301' disposed around the surface of upper mandril 320, and lower mandrils 330, 330', respectively. Balloon-expandable aortic and iliac stents are, in turn, placed around the balloons. When assembly 310 is properly placed near the aneurysm, balloon 300 underneath the balloon expandable stent 350 in the aorta is inflated via inlet 390, thus increasing the size of the aortic stent and locking the proximal end 371 of the graft 370 in place. The balloon expandable iliac stents 360, 360' are then expanded so as to deploy the iliac stents 360, 365 and secure the distal ends of the graft. Thereafter, balloons 300, 301 301' are deflated and the entire mandril assembly 310 is removed through the subclavian 1.

Figure 6:
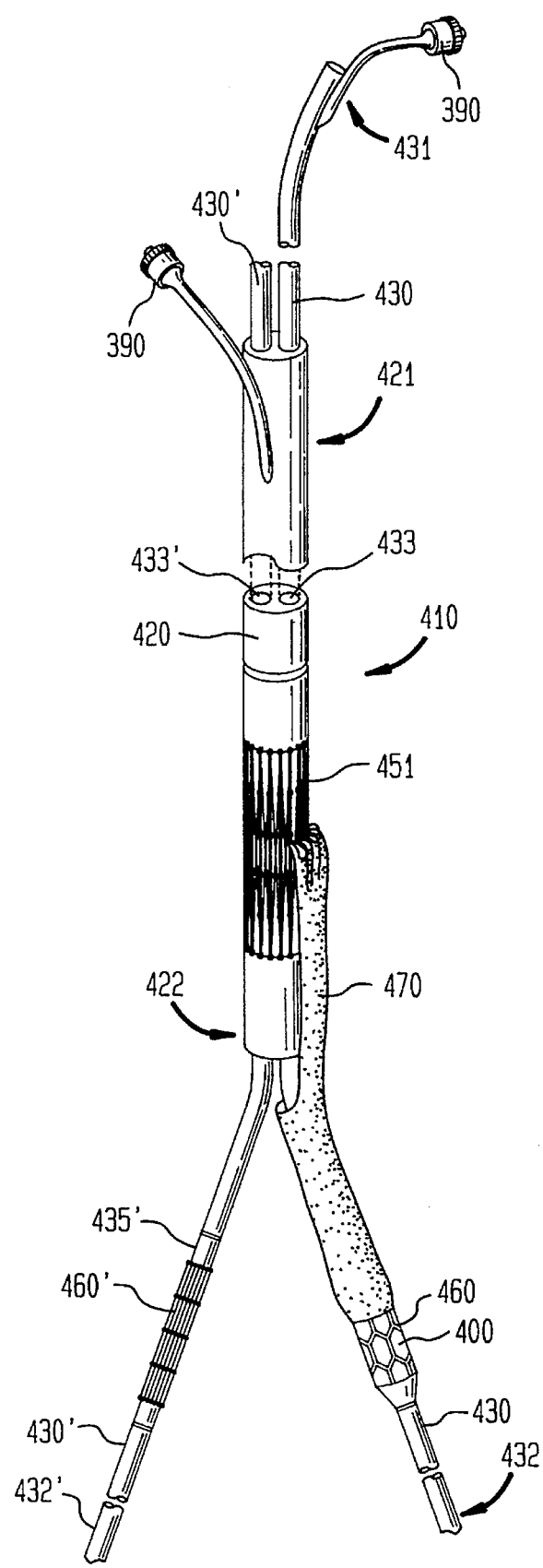
FIG. 6 is a view, in partial cross-section of a bifurcated mandril including balloon expandable stents and slidable lower mandrils.

In yet another preferred embodiment shown in FIG. 6, the lower mandrils 430, 430' of assembly 410 are slidably disposed within and through upper mandril 420. In other words, rather than being in a fixed position with the upper mandril, the lower mandrils slide through the upper mandril. Within upper mandril 420 are two channels 433, 433' extending from proximal end 421 to distal end 422. Lower mandrils 430, 430' extend through these tubes, such that the proximal end 431 of lower mandril 430 extends above the proximal end 421 of upper mandril 420, and distal end 432 of lower mandril 430 extends below the distal end 422 of upper mandril 420. In operation, once the aortic stent 451 is in position and deployed, the individual iliac stents 460, 460' are positioned by pushing and pulling on the proximal ends 431, 432, 432' which extend out of the body of the patient. One advantage of this arrangement is that all of delicate work of carefully positioning the graft can take place in the same end of the patient, i.e., at the proximal end. It may be advisable for this arrangement to include a stop mechanism located a certain distance proximal to the upper end 421 of the upper mandril 420 to ensure that the lower mandrils 430, 430' are not pulled too far so as to rip the stent or withdraw the lower mandrils out of the upper mandril. On the other hand, the stop may be configured to allow for withdrawal of the lower mandrils 430, 430' through the femoral artery 5 when desired. Alternatively, rather than passing the lower mandrils completely through the upper mandrils, it is possible to dispose the proximal end 431 of the lower mandril 430 below the distal end 422 of the upper mandril 420, and then run a rigid wire from the proximal end 431 of the lower mandril 430 up through the channels 433, 433' of the upper mandril 420.

These embodiments can be used either with or without guide wires as previously described. In addition, the device illustrated in FIG. 6 may be particularly useful in performing surgery without the use of incisions in the femoral arteries. Specifically, an incision can be made in the subclavian as previously described and a bifurcated mandril assembly 410 inserted as previously described. The distal ends 432, 432' of the assembly 410, in one embodiment, will be attached to, embedded in or include floatation devices which will allow them to float independently into the two iliac arteries. Alternatively, the distal ends 432 and 432' of the lower mandrils 430 and 430' can be tapered and may include somewhat converging conical tips which form something of a claw shape when positioned in opposition to each other. After mandril assembly 410 is inserted into the subclavian, the lower mandrils could be rotated from the proximal end of the assembly such that the tips 432, 432' diverge to assist in feeding the individual iliac ends of the graft into the respective iliac arteries. In such an arrangement, housings 434 and 434' would be anchored in some way to the body of the upper mandril 420 to prevent the graft 470 from rotating when mandrils 430, 430' are rotated.

In another embodiment, guide wires can be fed into the iliac and femoral arteries as previously described. However, no incisions are made to retrieve same through the legs. Thereafter, the mandril assembly 410 is threaded onto the guide wires 411 and 412 and, generally pushed into position from above. Once the graft 470 has been properly placed and fixed, both the mandril and the guide wires can be removed through the subclavian 1.

FIG. 6 also shows a combination of stent deployment methods. For example, a balloon is used to deploy the iliac stents 460, 460' and a self-expanding stent 70 is used in the aorta. Nearly any combination of stents is possible in accordance with the present invention.

These surgical methods are not limited to only an approach, which introduces the graft through the subclavian. In fact, any entry point or access point which may be provided above the iliac divide and above the junction between the abdominal aorta 3 and the renal arteries 2 can be used. Thus, the axillary artery can be used as can the descending thoracic aorta if, for example, the patient were already on the operating table having open heart or heart bypass surgery. Further, a distal approach may also be used.

As shown in FIGS. 13, 14, mandril assembly 510 is preferably used if a distal approach is selected. While the mandril assembly 510 used in a preferred aspect of the invention is very similar in structure to the mandril assembly 10 previously described, there are some differences. As illustrated in FIG. 14, the graft carrying assembly 510 is placed on the guide wires 511, 512 so that subclavian guide wire 512 is fed through the aortic or proximal end 521 of the upper mandril 510 and through one of lower mandrils 530'. This lower mandril 530' is also referred to as the first iliac end. Thus, the guide wire 512 is fed through the aortic end of the graft 570 and out through the first iliac end thereof. As shown in FIG. 13, lower mandril 530' will remain in the insertion leg and more particularly, in the first iliac artery 505'. The "cross-over" or second guide wire 511 is fed into the "cross-over" or lower mandril 530 through its distal end 532 and again out through the distal end 532' of mandril 530' of the assembly 510. Mandril 530 is also referred to herein as the second iliac end. Thus, the second guide wire 512 is fed though both iliac ends of graft 570.

In most other respects, the distal assembly 510 is substantially the same as the proximal assembly 10 previously described. However, as shown in FIG. 14, the upper assembly 520 may be, and preferably is, integrally formed with lower mandril 530' and is generally not detachable therefrom. Of course, it is possible that upper mandril 520 and lower 530 are detachable through some sort of detachable coupling as previously described. In the configuration illustrated in FIG. 14, upon deployment of the graft, the upper mandril 520 and lower mandril 530' will be removed as a single unit through one of the iliac arteries as further described herein. Otherwise, a detachable coupling device is attached around the proximal end 531' of lower mandril 530' and the upper mandril will be removed through the subclavian with the lower mandril 530' being removed through the first iliac artery.

Lower mandril 530 is preferably attached to the proximal end 531' of the first lower mandril 530'. However, as illustrated in FIG. 14, as upper mandril 520 and lower 530' are essentially one piece, lower mandril 530 may also be considered to be connected to the distal end 522 of upper mandril 520. Preferably, distal mandril 530 is attached to the remainder of the assembly 510 through a detachable coupling member 525 as previously described. In FIG. 14, the detachable coupling includes a threaded receiving member 525 and a threaded male member 525'. Moreover, in a preferred embodiment, a flexible bridge member 575 is disposed to assist assembly 510 and in particular, cross-over mandril 530 in being properly positioned in the second iliac artery and in taking up the substantially "Y" shape required for proper placement of graft 570.

As shown in FIG. 13, in operation, a single wire 512 is run from the subclavian 1 to the leg through which the assembly will be inserted, i.e. common femoral artery 505'. Retrieval of the guide wire 512 is through a transverse arteriotomy as before. Next, BEUAS 5200 is inserted into the common femoral artery 505' along the subclavian guide wire 512. A transverse arteriotomy is performed in the second or opposite common femoral artery 505 and a second guide wire 511 is passed through the BEUAS 5200 and out of the body through the other common femoral artery. Thus, while guide wire 512 runs from the subclavian 1 to the first iliac artery and protrudes therefrom, guide wire 511 runs from the first iliac artery to and through the second iliac artery with one end of guide wire 511 protruding from each of the patient's legs. The reverse can also be accomplished with the end of the cross-over guide wire being snared and brought out through the BEUAS 5200. Guide wires 511 and 512 can be inserted in the reverse order as well.

Next, with the guide wires 511, 512 fed through mandril assembly 510 as described above, both the proximal end 521 of the upper mandril 520 and the distal end 532 of cross-over mandril 530 are advanced through the BEUAS 5200 until the upper end 521 emerges and protrudes from the subclavian 1 and the distal end 532 of the cross-over mandril 530 emerges and protrudes from the femoral artery. As can be seen in FIG. 14, the junction of the upper and lower mandrils are not completely parallel to one another; rather, cross-over lower mandril 530 extends at an obtuse angle from the Other lower mandril 530' and at an acute angle to upper mandril 520. This angled rest position enables the assembly to more easily conform to the arterial structure of the patient. Thereafter, the main portion of the assembly 510 including the graft 570 is fed into the first iliac artery 505' with both the aortic end 571 and second iliac end 572 of the graft being advanced ahead of the first iliac 572' end of the graft. Eventually, the aortic stent 550 will be brought into place along guide wire 512 above aneurysm 506 and below the junction with the renal arteries 502. At the same time, the distal assembly 530 will continue along guide wire 511 crossing over the iliac divide and entering the second iliac artery for placement therein. Finally, the first iliac end of the graft 572' housed on distal mandril 530' will be dragged essentially backwards into place in the iliac artery 505.

Once the graft 570 is in position, only the cross-over lower mandril 530 need be detachable as previously described, although the upper mandril 520 for placing the aortic stent 550 in place may also be detached so as to be removable through the subclavian 501. One possible detachable coupling means is shown in FIG. 14 whereby a portion of detachable coupling means 525 is disposed at the proximal end 531 of cross-over mandril 530 while the other portion 525' is disposed at the proximal end 531' of lower mandril 530'. As described above in connection with other preferred embodiments, the aortic stent 550 is positioned first by manipulating the protruding ends of the mandrils. If a detachable mandril 520 is used for the upper portion of the graft 570, then the upper mandril 520 can be removed through the subclavian artery. Otherwise, mandril 520 is left in place. Next, by manipulating ends 532, 532' of the lower mandrils, the iliac stents 560, 560' are positioned in place. The cross-over mandril is then detached and removed through the femoral artery 505.

As shown in FIG. 14a, it is also possible that the bifurcated mandril in accordance with the present invention be discontinuous. For example, mandril 530 could be totally independent of mandril 520 and mandril 530' essentially eliminating coupling member 525 and bridge 575. The proximal end 531 of distal mandril 530 will therefore be free, albeit disposed within graft 570. In essence, mandril 530 is retained in communication and cooperation with the remaining assembly 510 via graft 570 which is anchored, via stents 550, 560 and 560' as well as sheaths 581, 582 and 582'. Care should be taken to ensure that the distal end 532 of mandril 530 is carefully manipulated so that graft 570 is not twisted upon delivery. Discontinuous mandrils can also be used in the proximal approach as described herein previously.

In an alternate embodiment, it is possible to eliminate the need for an access point in the subclavian artery 1 or any other point above the junction of the abdominal aorta 3 and the renal arteries 2. This may be accomplished by using a relatively shorter guide wire 512 which will dangle within the abdominal aorta or thereabove or by eliminating guide wire 512 completely. Because of the configuration of the distal mandril assembly 510, upper mandril 520 will naturally fall into place in the abdominal aorta and the relative position of aortic stent 550 can be adjusted by manipulating the distal ends 532 and 532' of lower mandrils 530 and 530'. This would be particularly useful when using a device as shown in FIG. 15 which employs balloon expandable stents as there will be no need to employ a sheath around stent 550. If, however, a self expanding stent is used, a pre-split sheath will accommodate withdrawl over the crossover mandril.

It is also possible to use balloon inflatable stents in the distal surgical procedure as well. As shown in FIG. 15, an assembly which is essentially of the same construction as that illustrated in FIG. 14 is provided. However, the aortic stent 850 and the iliac stent 860 which will be deployed in the insertion leg of the patient, in this case, are balloon expandable stents which will be deployed by the input of air or a gas into inlets 890 and 891 respectively to inflate balloons 8100 and 8101 respectively. In using balloon expandable stents and mandrils which can accommodate same, it is not necessary that sheaths be used. However, some form of sheath or outer covering may be desirable to ease insertion and minimize trauma.

It is also possible in accordance with this aspect of the present invention to produce assemblies with combinations of balloon and self-expandable stents. In the embodiment pictured in FIG. 15, the cross-over stent remains as previously described with regard to the embodiment in FIG. 14 utilizing a self-expanding stent 860' and a removable sheath 882'. A self-expanding stent is generally preferred for the cross-over assembly because it is somewhat more complicated to inflate a balloon through the bend in the cross-over mandril 830'. Of course, it could be inflated through a valve disposed at the mandril's distal end 832'. In this embodiment, distal or iliac mandril 830' is withdrawn through the femoral artery of one leg and the remaining assembly including upper mandril 820 and iliac mandril 830 are withdrawn through the femoral artery in the other leg.

Self expanding stents and balloons may also be used in a more direct combination. For example, with reference to FIG. 19 housing 3400 may be so constructed as to have a balloon 3700 within recess 3500 disposed underneath or inside of self expanding iliac stent 360. The balloon 3700 can communicate via an air inlet 3900 and passage way 3800 built into housing 3400 or mandril 3000 to a gas inlet 4000 near the distal end of mandril 3000. When a sheath (not shown) is retracted, self expanding stent 3600 will expand and be deployed within the iliac artery essentially tacking the iliac end of a graft (not shown) in place. However, it may be desirable to further expand the self expanding stent 3600 to insure the degree of engagement between the stent, graft and the iliac wall is sufficient. In that instance, gas may be fed in through the inlet 4000 at the distal end of mandril 3000 which will inflate the balloon 3700 contained in recess 3500. The balloon 3600 can then expand and further expand stent 3600. Thereafter, the balloon is deflated and surgery progresses as described herein. Such balloons can be used to assist the deployment of the other iliac stent and/or the aortic stent as need be.

As previously described with regard to other constructions, it is not necessary that guide wires be used in accordance with this aspect of the present invention. For example, using an extended mandril or a hybrid mandril as previously described, a long mandril can be fed through the BEUAS, up the femoral and iliac arteries, into the aorta and out through the incision in the subclavian artery. The second mandril, this one attached to the cross-over leg as opposed to the upper portion of the graft, may be fed into the aorta just above the divide of the iliac arteries and snared through the incision in the common femoral artery of the other leg and pulled back therethrough.

Alternatively, in both the subclavian and groin entry protocols, it may be possible to use a device which employs one hollow mandril to accommodate a guide wire running from the subclavian out through One of the common femoral arteries in one of the legs as well as an elongated mandril attached to one of the bifurcated legs of the assembly carrying one of the bifurcated legs of the graft.

No matter which device as described herein is used and no matter whether the entry approach is through the neck or through the groin, certain attributes of the present invention should be apparent. Most notably, the surgeon has direct control, simultaneously, over each end of the bifurcated graph. This can only be accomplished by the use of a series of entry points or incisions on each side of the afflicted portion of the aorta and iliac arteries and the provision of a device, with or without guide wires, that simultaneously extends out of the body through all three entry points so as to allow a surgeon manipulate every end of the bifurcated graft.

Further, because the present invention preferably allows control over all three ends of the graft (as compared to traditional approaches where one of the iliac ends is usually left to dangle during positioning of the other two ends) and preferably all three ends of the graft and mandril can be directly manipulated from outside of the body, the surgeon will have no trouble getting the both iliac ends into the appropriate position.

In addition, because guide wires in accordance with the present invention only act as tracks for the graft and various delivery assemblies, the wires can be much thinner than those traditionally used in similar operations. For example, wires ranging from a thickness of about 0.18 to about 0.020 may be used. (Currently, the thinnest wire used is about 0.038 gauge wire.)

As described above, nearly any stent may be used in accordance with the present invention. However, one possible self-actuating stent is shown in FIG. 16. The stent is generally cylindrical, and is comprised of two interwoven metal or alloy wires 601 and 603. The wires are made of a material such as Titanium, stainless steel, or known memory materials, which returns to its original shape after reasonable deformation. Wire 601 is a closed loop which zigzags back and forth to define a generally hollow cylindrical boundary, wherein portions of the wire extend from one planar edge of the cylindrical boundary to the other planar edge of the cylindrical boundary, and wherein such portions of the wire are generally at an angle to the planes defined by such planar edges. In other words, wire 601 forms a set of consecutive triangles extending around the surface of a cylinder, with the apex 609 of alternating triangles reaching the top plane 605 of the cylinder and the opposing side of the triangles being open and at the bottom plane 607 of the cylinder.

Stent 600 also includes a second wire 603 having a nearly identical structure to wire 601. However, for every apex 609 of the first wire 601 at the top 605 of the cylinder, there is an apex 611 of the second wire 603 directly opposite apex 609 at the bottom 607 of the cylinder. The two wires 601 and 603 intersect one another midway between the top 605 and bottom 607 planes at a plurality of points 613. Wire 601 remains straight and wire 603 loops around wire 601 in alternating directions forming a loop at midpoint 613. At midpoint 613, wire 601 may have a short portion which is parallel to the top and bottom planes 605, 607 level in order to facilitate the connection. The size of the loop should be sufficient to pass not only wire 601, but also to pass a suture thread. Thus, a surgeon can suture a graft to stent 600 by attaching the graft to the stent at midpoints 613.

The apices 609, 611 preferably do not lie in the same cylindrical surface generally defined by the stent. Rather the apices extend farther outward and away from the center of the cylinder than the rest of the stent. The extended apices in the configuration shown allow for the elimination or minimization of metal fatigue or stress, particularly when compared to stents which may be formed with hard corners. This structure also helps to maintain dynamic tension over a longer periods of time. Rather than crimping the stent at the apices, it is preferable that the apices be somewhat bulbed shaped to aid the performance of the stent as it expands from its contracted position.

As shown in FIG. 17 the balloon expandable universal access sheath or ("BEUAS") 2000 is a universal entry port which may be used in accordance with the surgical methods described herein, as well as any other type of surgical procedure which requires entry into a blood vessel such as an artery or a vein. The use of the BEUAS is certainly not limited to aortic grafting.

BEUAS 2000 comprises a housing 2100 which can be of any shape and cross-section. The generally hollow housing includes an opening at its top into which is placed a diaphragm 2120 (preferably a silicon diaphragm). Diaphragm 2120 preferably contains a central aperture 2140. Disposed within the interior of the housing is a tricuspid valve 2160 (also preferably of silicon or silicon rubber) which, as illustrated in FIG. 17, is a valve comprised of several downward curving or downward extending flaps. Valve 2160 is similar in construction to the tricuspid valve found in the heart. Of course, while a tricuspid valve is illustrated, a two part, four part or other multi-part valve, or its equivalent may also be used. In fact, any valve 2160 or diaphragm 2120 which can perform the functions described herein would be acceptable.

A chamber 2180 is defined between diaphragm 2120 and tricuspid valve 2160. Preferably, access to chamber 2180 is provided via outlet 2200. A second chamber 2220, disposed below tricuspid valve 2160 is also defined. Attached and/or formed integrally with chamber 2220 is a balloon expandable sheath 2260. Sheath 2260 may be composed of a balloon expandable stent having sheath material sutured thereto. However, preferably, the sheath is composed of a weave of cloth and metal material which will expand when a balloon is inserted therein and expanded, just as a balloon expandable stent would. The stent material is disposed longitudinally within the fabric.

BEUAS 2000 cooperates with a balloon insertion device 2300 illustrated in FIG. 18. Device 2300 comprises an air or gas inlet 2310 which feeds air into a handle 2320, down an elongated support rod 2330 and finally into an expandable, non-compliant balloon 2340 disposed around support rod 2330. The balloon 2340 is selected to have a predetermined size and shape upon inflation. Thus balloon 2340 controls the resulting size of the access provided through access 2260 in BEUAS 2000. Preferably, device 2300 is provided with an insertion tip 2350 which will make its insertion into the BEUAS 2000 and into the body easy, without the possibility of damaging various blood vessels.

In operation, device 2300 is inserted into the BEUAS by inserting tip 2350 through aperture 2140 into and through chamber 2180 and into engagement with tricuspid valve 2160. Tricuspid valve 2160 will be pushed away or parted such that the balloon 2340 and stem 2330 of device 2300 can be inserted into expandable sheath 2260. Both devices are then inserted into a blood vessel such as an artery or vein through an incision. Gas is then fed through inlet 2310 through device 2300 and into balloon 2340 whereupon balloon 2340 expands to a predetermined shape and diameter. In so doing, the metal contained within sheath 2260 is deformed and expanded to increase its diameter. The external surface of sheath 2260 generally comes into contact with the walls of the access blood vessel and may stretch that vessels in diameter by up to about 20%. Thereafter, balloon 2340 is deflated and device 2300 is withdrawn from the BEUAS 2000. By removing same, the various members of the tricuspid valve are allowed to return to their original position. The sheath protects the blood vessel and also allows for the straight and uniform insertion and removal of devices, such as the mandril assemblies of the present invention.

In a preferred embodiment, the device 2300 is hollow or is provided with a channel 2360 to allow it to be inserted over a guide wire (not shown).

During surgery, it is not uncommon for there to be some bleeding through the access way or the access incision. By use of the BEUAS, such bleeding can be retarded. Moreover, to the extent that blood collects in chamber 2220 or 2180 that blood can be aspirated or removed using a light suction, cleaned and returned to the body of the patient. The BEUAS may also be secured to the body through use of a suture hold 2240 or other similar structure.

The principles, preferred embodiments and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention.

What I claim is:

1. A method of implanting an abdominal aortic graft into the body of a patient, said patient having an abdominal aorta which has an interior and an exterior, said abdominal aorta being joined at a proximal end by at least one renal artery and said abdominal aorta being joined at a distal end to a first and a second iliac artery, said first and said second iliac arteries having interiors and exteriors and being in fluid communication with said abdominal aorta said first and said second iliac arteries joining said abdominal aorta so as to form a divide and said divide being disposed distal to the junction of said abdominal aorta and said renal artery which is disposed above said divide, comprising the steps of:

providing access through first and second access points to open said interior of said first and second iliac arteries of said patient; providing access through a third access point to said interior of said abdominal aorta above said iliac divide and above said junction between said aorta and said renal artery of said patient;

introducing a bifurcated graft having an abdominal end, a first iliac end, and a second iliac end into said abdominal aorta and said iliac arteries through one of said access points;

positioning said bifurcated graft by manipulating said graft through at least said third access point and at least one of said first or said second access points;

and fixing said bifurcated graft in place.

2. The method of claim 1 wherein said bifurcated graft is introduced through said third access point.

3. The method of claim 1 wherein said bifurcated graft is introduced through said first or said second access point.

4. The method of claim 1 further comprising the step of manipulating each end of said bifurcated graft to position said bifurcated graft in the abdominal aorta and the first and second iliac arteries prior to fixing said bifurcated graft in place.

5. The method of claim 1 further comprising the step of placing at least a first guide wire through both said third access point and said first access point, wherein both ends of said first guide wire protrude from said body of said patient.

6. The method of claim 5 further comprising the step of placing a second guide wire through both said third access point and said second access point, wherein both ends of said second guide wire protrude from said body of said patient.

7. The method of claim 6 further comprising running said first and said second guide wires through a supraclavicular left subclavian artery.

8. The method of claim 5 further comprising the step of running a second guide wire through both said and said second access points, wherein both ends of said second guidewire protrude from said body of said patient.

9. The method of claim 8 further comprising running said first guide wire through the supraclavicular left subclavian artery.

10. The method of claim 6 further comprising the steps of threading said first iliac end of said bifurcated graft on said first guide wire and said second iliac end of said bifurcated graft on said second guide wire, and threading both said first and said second guide wires through said aortic end of said bifurcated graft, wherein said bifurcated graft is introduced into the abdominal aorta and iliac arteries by following the course set by said guide wires.

11. The method of claim 8 further comprising the steps of threading said first guide wire through said first iliac end and said aortic end of said bifurcated graft and said second guide wire through said first and said second iliac ends of said bifurcated graft.

12. A method of implanting a bifurcated graft into a bifurcated blood vessel within the body of a patient, said vessel having a first and a second hollow member which merge into a third hollow member, said first, second and third hollow members of said vessel being in fluid communication, comprising the steps of:

providing access through a first access point to the interior of said first hollow member providing access through a second access point to the interior of said second hollow member and providing access through a third access point to the interior of said third hollow member;

introducing into said first hollow member through said first access point a bifurcated mandril assembly having a first end, a second end and a third end said bifurcated mandril assembly including a bifurcated graft, by inserting said third end and said second end of said mandril assembly into said first hollow member, before introducing said first end of said mandril assembly into said first hollow member;

manipulating said first and said second ends of said mandril assembly into place in the first and second hollow vessels respectively in such a way as to position said third end of said mandril assembly in the third hollow member; and fixing said bifurcated graft in place.

13. The method of claim 12 further comprising the steps of introducing a first guide wire into said first hollow member through said first access point;

feeding said first guide wire into said third hollow member; and threading said third end and said first end of said bifurcated mandril on said first guide wire, prior to the step of introducing said mandril assembly into said first hollow member through said first access point.

14. The method of claim 13 further comprising the steps of introducing a second guide wire into said first hollow member through said first access point;

feeding said second guide wire through to the second hollow member and out of the body of the patient through said second access point; and threading said second end and said first end of said bifurcated mandril on said second guide wire prior to the step of introducing said mandril assembly into said first hollow member through said first access point.

15. The method of claim 12 further comprising the step of removing at least a portion of said mandril assembly through at least said first hollow member.

16. The method of claim 15 further comprising the step of removing said third end and said first end of said mandril assembly through said first hollow member and removing said second end of said mandril assembly through said second hollow member.

17. The method of claim 12, wherein said bifurcated mandril assembly is continuous.

18. A method of implanting a bifurcated graft into a bifurcated blood vessel within the body of a patient, said vessel having a first and a second hollow member which merge into a third hollow member, said first, second and third hollow members of said bifurcated vessel being in fluid communication, comprising the steps of:

providing access through a third access point to the interior of said third hollow member;

introducing into said third hollow member a bifurcated mandril assembly having a first end, a second end and a third end, said bifurcated mandril assembly including a bifurcated graft, by inserting said first end and said second end of said mandril assembly into said third hollow member through said third access point, before introducing said third end of said mandril assembly therethrough;

manipulating said mandril assembly into place such that said first end of said bifurcated mandril is disposed in said first hollow member, said second end of said bifurcated mandril is disposed in the second hollow member, and said third end of said mandril assembly is disposed in said third hollow member; and fixing said bifurcated graft in place.

19. The method of claim 18 wherein said step of manipulating said mandril assembly includes independently manipulating said first end, said second end and said third end of said mandril assembly.

20. The method of claim 18 further comprising the step of introducing a first guide wire into said third hollow member through said third access point and feeding said first guide wire into said first hollow member;

introducing a second guide wire into said third hollow member through said third access point and feeding said second guide wire into said second hollow member;

threading said first end and said third end of said mandril assembly on said first guide wire and threading said second end and said third end of said mandril assembly on said second guide wire, prior to said step of introducing said mandril assembly into said third hollow member; and introducing said mandril assembly into said bifurcated vessel by following said first and said second guide wires.

21. The method of claim 18 further comprising the step of providing access through a first access point to the said first hollow member and retrieving the first end of said bifurcated mandril through said first access point such that both the third end and first end of said mandril assembly protrude from said body of said patient such that said mandril assembly may be directly manipulated.

22. The method of claim 21 further comprising the step of providing access, through a second access point to the said second hollow member and retrieving the second end of said bifurcated mandril assembly through said second access point such that the third end, first end, and second end of said mandril assembly protrude from said body of said patient such that same may be directly manipulated.

23. The method of claim 22 further comprising the steps of:

prior to introducing said mandril assembly into said third hollow member;

introducing a first guide wire into said third hollow member through said third access point and feeding said first guide wire into said first hollow member and out of body of said patient through said first access point;

introducing a second guide wire into said third hollow member through said third access point and feeding said second guide wire into said second hollow member and out of said body of said patient through said second access point;

threading said first end and said third end of said mandril assembly on said first guide wire and threading said second end and said third end of said mandril assembly on said second guide wire; and introducing said mandril assembly into said third hollow member through said third access point following said first and said second guide wires.

24. The method of claim 18 further comprising the step of removing said bifurcated mandril through said third access point.

25. The method of claim 22 further comprising the step of removing a portion of the mandril assembly through each of the first, second and third access points.

26. The method of claim 18, wherein said bifurcated mandril assembly is continuous.

* * * * *

UNITED STATES PATENT AND TRADEMARK OFFICE
CERTIFICATE OF CORRECTION

PATENT NO.   :   5,591,228
DATED        :   January 7, 1997
INVENTOR(S)  :   Edoga It is certified that error appears in the above-identified patent and that said Letters Patent is hereby corrected as shown below:

```
Column 9, line 50, please insert --is-- immediately after
"vein"
Column 11, line 1, "anglogram" should read --angiogram--
Column 15, line 26, "Other" should read --other--
Column 17, line 22, "One" should read --one--
Column 19, line 66, please delete --open--
Column 20, line 35, please insert --first-- immediately after
"both said"
Column 21, line 1, please insert --,-- immediately after "third
end"
Column 22, line 33, please delete "same" and insert in its place
--said mandril assembly--
Column 22, line 44, please insert --the-- immediately after "out
of"
```

Signed and Sealed this

Eighth Day of April, 1997

*Attest:*

BRUCE LEHMAN

*Attesting Officer*    Commissioner of Patents and Trademarks